United States Patent
Drucker et al.

(10) Patent No.: US 8,257,653 B2
(45) Date of Patent: Sep. 4, 2012

(54) CENTRAL SERVER SYSTEM FOR COLLECTING PATIENT HEALTH CONDITION MANAGEMENT DATA

(75) Inventors: Steven Drucker, Oakland, CA (US); Charles T. Liamos, Pleasanton, CA (US); Fredric C. Colman, Oakland, CA (US); Mark Lortz, Pleasanton, CA (US); Kelley Lipman, Livermore, CA (US); Feng Jiang, Union City, CA (US); Henrik Bacho, San Francisco, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

(21) Appl. No.: 12/776,362

(22) Filed: May 7, 2010

(65) Prior Publication Data

US 2011/0125530 A1    May 26, 2011

Related U.S. Application Data

(63) Continuation of application No. 11/160,407, filed on Jun. 22, 2005, now Pat. No. 7,976,778, which is a continuation of application No. 10/112,671, filed on Mar. 29, 2002, now Pat. No. 7,041,468.

(60) Provisional application No. 60/300,011, filed on Jun. 20, 2001, provisional application No. 60/280,905, filed on Apr. 2, 2001.

(51) Int. Cl.
*G01N 33/00* (2006.01)

(52) U.S. Cl. .......... 422/68.1; 422/50; 422/401; 422/402

(58) Field of Classification Search ................. 422/68.1, 422/50, 401, 402
See application file for complete search history.

(56) References Cited

U.S. PATENT DOCUMENTS

| | | | |
|---|---|---|---|
| 5,558,638 | A | 9/1996 | Evers et al. |
| 5,673,691 | A | 10/1997 | Abrams et al. |
| 5,678,571 | A | 10/1997 | Brown |
| 5,704,366 | A | 1/1998 | Tacklind et al. |
| 5,772,586 | A | 6/1998 | Heinonen et al. |
| 5,778,882 | A | 7/1998 | Raymond et al. |
| 5,822,715 | A | 10/1998 | Worthington et al. |
| 5,827,180 | A | 10/1998 | Goodman |
| 5,899,855 | A | 5/1999 | Brown |
| 5,902,234 | A | 5/1999 | Webb |
| 5,933,136 | A | 8/1999 | Brown |
| 5,954,641 | A | 9/1999 | Kehr et al. |
| 5,956,501 | A | 9/1999 | Brown |
| 5,967,975 | A | 10/1999 | Ridgeway |
| 5,991,729 | A | 11/1999 | Barry et al. |

(Continued)

FOREIGN PATENT DOCUMENTS

DE    10042101 A1    2/2002

(Continued)

*Primary Examiner* — Sam P Siefke
(74) *Attorney, Agent, or Firm* — Thomas A. Runk; Fulwider Patton LLP

(57) ABSTRACT

A measurement module for glucose testing includes a glucose testing measurement module housing, a test strip receptacle formed in the housing, and a connector portion formed in the housing and shaped to permit mechanical removable attachment of the housing to a hand-held computer. Electronics determine the amount of glucose present in a sample of body fluid, when the test strip is positioned in the receptacle and the body fluid is placed on a test strip, and communicate the glucose amount to the hand-held computer via the connector portion.

27 Claims, 19 Drawing Sheets

U.S. PATENT DOCUMENTS

| | | | |
|---|---|---|---|
| 6,039,688 A | 3/2000 | Douglas et al. | |
| 6,161,095 A | 12/2000 | Brown | |
| 6,167,362 A | 12/2000 | Brown et al. | |
| 6,171,237 B1 | 1/2001 | Avitall et al. | |
| 6,249,809 B1 | 6/2001 | Bro | |
| 6,292,783 B1 | 9/2001 | Rohler et al. | |
| 6,389,461 B1 | 5/2002 | Shah | |
| 6,454,705 B1 | 9/2002 | Cosentino et al. | |
| 6,519,241 B1 | 2/2003 | Theimer | |
| 6,546,232 B1 | 4/2003 | Sack et al. | |
| 6,579,231 B1 | 6/2003 | Phipps | |
| 6,602,191 B2 | 8/2003 | Quy | |
| 6,645,142 B2 | 11/2003 | Braig et al. | |
| 6,648,821 B2 | 11/2003 | Lebel et al. | |
| 6,656,114 B1 * | 12/2003 | Poulsen et al. | 600/300 |
| 6,699,188 B2 | 3/2004 | Wessel | |
| 6,723,046 B2 | 4/2004 | Lichtenstein et al. | |
| 6,849,045 B2 | 2/2005 | Iliff | |
| 6,891,936 B2 | 5/2005 | Kai et al. | |
| 6,918,769 B2 | 7/2005 | Rink | |
| 7,077,806 B2 | 7/2006 | Ackermann et al. | |
| 7,287,031 B1 | 10/2007 | Karpf et al. | |
| 7,297,108 B2 | 11/2007 | Iliff | |
| 7,353,179 B2 | 4/2008 | Ott et al. | |
| 7,448,996 B2 | 11/2008 | Khanuja et al. | |
| 2001/0005830 A1 | 6/2001 | Kuroyanagi | |
| 2001/0051787 A1 | 12/2001 | Haller et al. | |
| 2002/0143241 A1 | 10/2002 | Thorell | |
| 2002/0186243 A1 | 12/2002 | Ellis et al. | |
| 2002/0188466 A1 | 12/2002 | Barrette et al. | |
| 2003/0101078 A1 | 5/2003 | Voegeli et al. | |
| 2004/0054263 A1 | 3/2004 | Moerman et al. | |
| 2004/0162035 A1 | 8/2004 | Petersen et al. | |

FOREIGN PATENT DOCUMENTS

| | | | |
|---|---|---|---|
| EP | 1416417 A2 | | 5/2004 |
| WO | WO 00/32258 | * | 6/2000 |
| WO | 0115056 A1 | | 3/2001 |
| WO | 0189362 A2 | | 11/2001 |
| WO | 02056151 A2 | | 7/2002 |
| WO | 02082984 A1 | | 10/2002 |
| WO | 03017832 A2 | | 3/2003 |
| WO | 03039361 A1 | | 5/2003 |

* cited by examiner

FIG. 6g  FIG. 6h

CENTRAL SERVER SYSTEM FOR COLLECTING PATIENT HEALTH CONDITION MANAGEMENT DATA

CROSS-REFERENCE TO RELATED APPLICATION

This application is a continuation of U.S. application Ser. No. 11/160,407 filed Jun. 22, 2005, now U.S. Pat. No. 7,976,778 which is a continuation of U.S. application Ser. No. 10/112,671 filed Mar. 29, 2002, now U.S. Pat. No. 7,041,468 which claims the benefit of U.S. Ser. No. 60/300,011 filed Jun. 20, 2001, and U.S. Application No. 60/280,905 filed Apr. 2, 2001, the entire contents of each is incorporated herein by reference.

BACKGROUND OF THE INVENTION

1. Field of the Invention

The invention relates to blood glucose monitoring, and particularly to a blood glucose monitor and data management and display device integrated as a synchronous, handheld unit, as an effective and efficient diabetes management tool.

2. Description of the Related Art

Blood glucose self-measurements have been conventionally taken by diabetics. The diabetic uses a blood glucose measuring tool. The diabetic typically pricks his or her finger using a lancet. A droplet of exposed blood is applied to a sensor strip which is placed in the glucose measuring tool. A reading appears on a display of the measuring tool indicating the blood glucose level of the diabetic.

Diabetics sometimes use a computer having some form of software that permits the user to track the glucose measurements they have taken. The glucose measurements are typically loaded into the computer manually by the diabetic. Other transfer methods are possible that require steps by the diabetic in order that the information gets entered into the computer, e.g., transferring glucose readings that have been retained in memory of the measuring tool via a cable to the computer. The data may be sent to a health care professional who may also be keeping an eye on the diabetic's status. It is an object of this invention to provide a more efficient and reliable process of taking the measurement, determining the glucose level, entering the glucose level data into a diabetes management program, and managing the diabetes condition using diabetes management software.

In the past, the glucose measurement tool could be carried by the patient for use almost anywhere. However, access to data entry and management using the computer and software have been relegated to a PC setup at a fixed location such as the patient's home, and so these steps had to wait until the diabetic arrived back at his or her home. In the present invention, it is recognized that the development of hand-held devices such as PDAs and mobile phones and PDA/mobile phone combined units could permit diabetics to enter data and use the data management software away from their PCs. It is therefore an object of this invention to provide a system that permits data entry and management by the diabetic away from the diabetic's PC. In addition, it is desired to have a device that permits this mobile data entry and management, and yet permits the user to take off-finger measurements, or using so-called alternate site testing.

Conventional methods have utilized two very separate instruments, the glucose measurement tool and the PC. It is an object of this invention to provide a synchronous tool that performs the conventional functions of both the glucose measurement tool and PC, and perhaps additional features and advantages. It is a further object to synergistically provide this tool, such as by using a same power source and/or a same display for both purposes, i.e., glucose measurement and data management and/or analysis.

SUMMARY OF THE INVENTION

In view of the above, and in particular accordance with the above objects, a measurement module for glucose testing is provided including a glucose testing measurement module housing, a test strip receptacle formed in the housing, and a connector portion formed in the housing and shaped to permit mechanical, removable attachment of the housing to a hand-held processing device, hand-held computer, PDA, mobile phone or wireless processing device. Electronics are provided either in the measurement module or in the hand-held processing device for determining the amount of glucose present in a sample of body fluid, when a test strip is positioned in the receptacle and the fluid is placed on the test strip, and for communicating the glucose amount to the processing device via the connector portion.

The test strip is typically inserted into the test strip receptacle so that the system may calibrate in preparation for application of the body fluid to the strip. Insertion of the strip may further initiate an activation of electrical components that participate in the testing of a body fluid sample. When the system is ready after connecting the measurement module with the hand-held processing device, and after insertion of the strip into the receptacle in the measurement module, and after any calibration or component activation, then the system display preferably indicates that the body fluid is to be now applied to the strip for testing. An alternative system may be or may become available to those skilled in the art wherein the body fluid is applied to the strip, and/or calibration/component activation occur, before strip insertion, and if such system would otherwise include one or more features of preferred embodiments herein, then such systems may also be within the scope of a preferred embodiment.

The housing of the glucose testing measurement module is configured so that a sample of body fluid may be easily applied to the strip when the module is connected to the hand-held processing device and the strip is inserted into the receptacle in the measurement module. The end of the housing from which the strip protrudes is substantially narrowed compared with the end that connects with the hand-held processing device. This narrowed end is preferably a tapered trapezoidal profile, is preferably rounded in two or three directions, protrudes from the connector end defining a shoulder or inset particularly for matching an alternate site body contour and is preferably made of low durometer material, so that the module can rest comfortably and securely on a body location near the test site for easy and precise application of the body fluid to the strip. This configuration of the housing is particularly advantageous when off-finger or alternate site testing is desired such as at an arm or a leg site.

The test strip may be side-filled and may also be tip-filled. Use of a side-filled strip is particularly advantageous for alternate site testing. For example, the module may be rested near the alternate test site (for example a forearm) with a user contacting a rounded shoulder of the housing on the user's skin. The device is then rocked comfortably into a test strip side-fill contact position with the body fluid, due to the ergonometric and/or arthopometric design of the module. For this purpose the module preferably has no square or sharp edges exposed when fitted with the handheld processing device. Even when using a tip-filled strip, exposed edges of the module are preferably rounded for rocking the strip into tip-filled contact with the body fluid, even though the depth of the module is small compared with its width particularly at the wider connection end, and contact with the user may be established perhaps only at a single point on the narrowed end when the body fluid in applied to the strip. The test strip advantageously uses only a relatively small amount of body fluid sample for performing reliable tests, such as less than 1 microliter. Measurements are conducted preferably using a coulometric technique, and alternatively an amperometric, reflectrometic or other technique understood by those skilled in the art, which is significant for alternate site testing wherein typically a lower volume of sample is made available by a same lancing operation at an alternate site than when testing is performed on the finger.

The removable connectability of the measurement module with the hand-held processing device is greatly facilitated by electronics that integrate the two components of this integrated system. An isolation barrier is provided for safe glucose monitoring and/or analysis, even though power is preferably supplied to the module from the hand-held processing device, while also data is transferred between the measurement module and hand-held processing device. The power is preferably transformer-coupled, or alternatively capacitively-coupled, between the isolated and non-isolated sides of the barrier. Analog front-end signal acquisition circuitry of the measurement module allows signals including data indicative of a blood glucose level or other test of the body fluid to be acquired by the measurement module. Opto-isolators preferably isolate data I/O circuitry and provide a data signal transport route across the barrier to the hand-held processing device so that the data can be analyzed there and/or easily uploaded to a PC by HotSync. By "HotSync", what is meant is any method of synchronizing data in the handheld with data in a PC, such as by cable, cradle, infrared or radio link. By "analyze", it is meant that the hand-held processing device can do more than merely display a glucose measurement value. For example, charts, plots and graphs of compiled glucose data can be generated and additional factors such as diet, exercise, insulin regimen, etc., may be used to process and/or display various information relating to a diabetic condition or regimen. Serial to parallel conversion circuitry permits parallel access to a data/address bus of the hand-held processing device to the data transported across the barrier.

In a particular embodiment, a measurement module for glucose testing is further provided including a test strip receptacle in a glucose measurement module, a connector portion formed in the module shaped to permit connection of the module to a hand-held computer by inserting the connector portion of the glucose measurement module into a receptacle defined within the hand-held computer, and electronics for determining the amount of glucose present in a sample of body fluid, when the fluid is placed on a test strip and the test strip is positioned in the receptacle, and for communicating the glucose amount to the hand-held computer via the connector portion.

A glucose monitoring apparatus is further provided including a measurement module configured to couple with a test sensor and a hand-held processing device electrically and mechanically coupled with the measurement module to form an integrated, hand-held unit for performing and analyzing a glucose measurement after the test sensor is coupled with the measurement module and body fluid is applied to the test sensor.

A further glucose monitoring apparatus is provided including a measurement module configured to couple with a test sensor and a hand-held processing device electrically and mechanically coupled with and separable from the measurement module to form an integrated, hand-held unit for performing and analyzing a glucose measurement after the test sensor is coupled with the measurement module and body fluid is applied to the test sensor.

A glucose monitoring apparatus is also provided including a measurement module configured to couple with a test sensor and a hand-held processing device configured to receive data transmission from the measurement module. The measurement module and processing device form a synchronous unit for performing and analyzing a glucose measurement after the test sensor is coupled with the measurement module and body fluid is applied to the test sensor. The monitoring apparatus includes a single display at the processing device.

A glucose monitoring apparatus is further provided including a measurement module not having a display for displaying results of glucose measurements, the module being configured to couple with a test sensor, and a hand-held processing device configured to receive data transmission from the measurement module. The measurement module and the processing device form a synchronous unit for performing and analyzing a glucose measurement after the test sensor is coupled with the measurement module and body fluid is applied to the test sensor. The processing device includes a display for displaying the results of said glucose measurements.

A glucose monitoring apparatus is further provided including a measurement module configured to couple with a test sensor and a hand-held processing device configured to receive a data transmission from the measurement module. The measurement module and processing device form a synchronous unit for performing and analyzing a glucose measurement. The processing device is configured for automatically receiving the data transmission after the test sensor is coupled with the measurement module and body fluid is applied to the test sensor.

A method of performing a glucose measurement using a measurement module and a hand-held processing device is provided including coupling the processing device electrically and mechanically with the measurement module to form an integrated, handheld unit for performing and analyzing a glucose measurement after a test sensor is inserted into the measurement module, coupling the test sensor with the measurement module, applying body fluid to the test sensor and reading a glucose level from a display on the integrated hand-held unit.

A method of performing a glucose measurement using a measurement module and a hand-held processing device is also provided including coupling the processing device with the measurement module to receive a data transmission from the measurement module such that the measurement module and the processing device form a synchronous unit including a single display on the processing device for performing and analyzing a glucose measurement after a test sensor is inserted into the measurement module, coupling the test sensor with the measurement module, applying body fluid to the test sensor and reading a body fluid glucose level from the display on the processing device.

A method of performing a glucose measurement using a measurement module and a hand-held processing device, is further provided including inserting the measurement module into a receptacle defined within the processing device for the processing device to receive a data transmission from the measurement module, such that the measurement module and the processing device form an integrated, hand-held unit for performing and analyzing a glucose measurement after a test sensor is inserted into the measurement module, coupling the test sensor with the measurement module, applying body fluid to the test sensor and reading a glucose level from a display on the processing device.

The invention further includes a method of performing a glucose measurement using a measurement module and a hand-held processing device including coupling the processing device with the measurement module to automatically receive a data transmission from the measurement module after a test sensor is inserted into the measurement module, such that the measurement module and the processing device form a synchronous unit for performing and analyzing a glucose measurement, coupling the test sensor with the measurement module, applying body fluid to the test sensor and reading a glucose level from a display.

A glucose monitoring apparatus is further provided including a measurement module configured to couple with a test sensor, and a hand-held processing device electrically and mechanically coupled with the measurement module to form an integrated, hand-held unit for performing and analyzing a glucose measurement after the test sensor is inserted and body fluid is applied to the test sensor. The measurement module is further geometrically configured to enable off-finger or alternate site application of blood to the test strip.

A glucose monitoring apparatus is also provided including a measurement module configured to couple with a test sensor, and a hand-held processing device electrically and mechanically coupled with the measurement module to form an integrated, hand-held unit for performing and analyzing a glucose measurement after the test sensor is inserted and body fluid is applied to the test sensor. The measurement module is rounded in three dimensions for providing smooth off-finger or alternate site points of contact with the skin of a person being tested.

A glucose monitoring apparatus is further provided including a measurement module configured to couple with a test sensor, and a hand-held processing device electrically and mechanically coupled with the measurement module to form an integrated, hand-held unit for performing and analyzing a glucose measurement after the test sensor is inserted and body fluid is applied to the test sensor. The measurement module is rounded in at least two dimensions for providing smooth off-finger or alternate site points of contact with the skin of a person being tested.

A glucose monitoring apparatus is also provided including a measurement module configured to couple with a test sensor, and a hand-held processing device electrically and mechanically coupled with the measurement module to form an integrated, hand-held unit for performing and analyzing a glucose measurement after the test sensor is inserted and body fluid is applied to the test sensor. The measurement module includes a telescoping trapezoidal profile for permitting placement of a test strip inserted within the module at an off-finger or alternate site location of a person being tested.

A glucose monitoring apparatus is also provided including a measurement module configured to couple with a test sensor, and a hand-held processing device electrically and mechanically coupled with the measurement module to form an integrated, hand-held unit for performing and analyzing a glucose measurement after the test sensor is inserted and body fluid is applied to the test sensor. The measurement module includes an encapsulation port for the test sensor and a PC board including an opto-isolation component. The measurement module extends less than two inches in length and less than one half inch in thickness beyond dimensions of the wireless processing device.

A software program for analyzing glucose data measured with a glucose monitoring apparatus which includes a measurement module configured to couple with a test sensor and a hand-held processing device is further provided. The measurement module and processing device form a synchronous unit for performing and analyzing a glucose measurement after the test sensor is inserted and body fluid is applied to the test sensor. The processing device is configured to HotSync with a PC. The software program includes instructions for a processor to perform the steps of creating a replica database on the PC of the glucose data stored in a device database on the processing device, and synchronizing the glucose data to a PC database program. The synchronizing step includes reading the glucose data stored in the device database on the processing device, matching the data to corresponding data in the replica database, format converting the data and writing the data to the replica database.

A software program for analyzing glucose data measured with a glucose monitoring apparatus which includes a measurement module configured to couple with a test strip and a hand-held processing device is also provided. The measurement module and processing device form a synchronous unit for performing and analyzing a glucose measurement after the test strip is inserted and body fluid is applied to the test strip. The processing device is configured to HotSync with a PC. The software program includes instructions for a processor to perform the steps of measuring glucose data from the test strip having body fluid applied thereto, automatically downloading the glucose data from the measurement module to the processing device, and downloading the glucose data to a personal computer.

A method for analyzing glucose data measured with a glucose monitoring apparatus which includes a measurement module configured to couple with a test sensor and a hand-held processing device. The measurement module and processing device form a synchronous unit for performing and analyzing a glucose measurement after the test sensor is inserted and body fluid is applied to the test sensor. The processing device is configured to HotSync with a PC. The method includes creating a replica database on the PC of the glucose data stored in a device database on the processing device, and synchronizing the glucose data to a PC database program. The synchronizing step includes reading the glucose data stored in the device database on the processing device, matching the data to corresponding data in the replica database, format converting the data, and writing the data to the replica database.

A method for analyzing glucose data measured with a glucose monitoring apparatus which includes a measurement module configured to couple with a test strip and a hand-held processing device is also provided. The measurement module and processing device form a detachably integrated, hand-held unit for performing and analyzing a glucose measurement after the test strip is inserted and body fluid is applied to the test strip. The processing device configured to HotSync with a PC. The method includes measuring glucose data from the test strip having body fluid applied thereto, automatically downloading the glucose data from the measurement module to the processing device after measuring said glucose data, and downloading the glucose data to a personal computer.

A software program for analyzing glucose data measured with a glucose monitoring apparatus which includes a measurement module configured to couple with a test sensor and a hand-held processing device is further provided. The measurement module and processing device form a synchronous unit for performing and analyzing a glucose measurement after the test sensor is inserted and body fluid is applied to the test sensor. The software program includes instructions for a processor to perform the steps of measuring glucose data, providing a sensory output of a glucose level corresponding to the data, and automatically entering the data into a database accessible by a diabetes management software program.

A method for analyzing glucose data measured with a glucose monitoring apparatus which includes a measurement module configured to couple with a test sensor and a hand-held processing device. The measurement module and processing device form a detachably integrated, hand-held unit for performing and analyzing a glucose measurement after the test sensor is inserted and body fluid is applied to the test sensor. The method includes measuring glucose data, providing a sensory output of a glucose level corresponding to the data, and automatically entering the data into a database accessible by a diabetes management software program.

BRIEF DESCRIPTION OF THE DRAWINGS

FIG. 6b schematically shows a rear view of the glucose module of FIG. 6a.

FIG. 6c schematically shows a bottom perspective view of the glucose module of FIG. 6a.

FIG. 6d schematically shows a top perspective view of the glucose module of FIG. 6a.

FIG. 6e schematically shows a side view of the glucose module of FIG. 6a.

FIG. 6f schematically shows a front view of the glucose module of FIG. 6a.

FIG. 6g schematically shows another side view of the preferred glucose module with preferred dimensions shown in millimeters.

FIG. 6h schematically shows a top view of the preferred glucose module with preferred dimensions shown in millimeters.

FIG. 7b schematically shows a plan view of the integrated measurement module and PDA of FIG. 7a.

INCORPORATED BY REFERENCE

Figure 1:
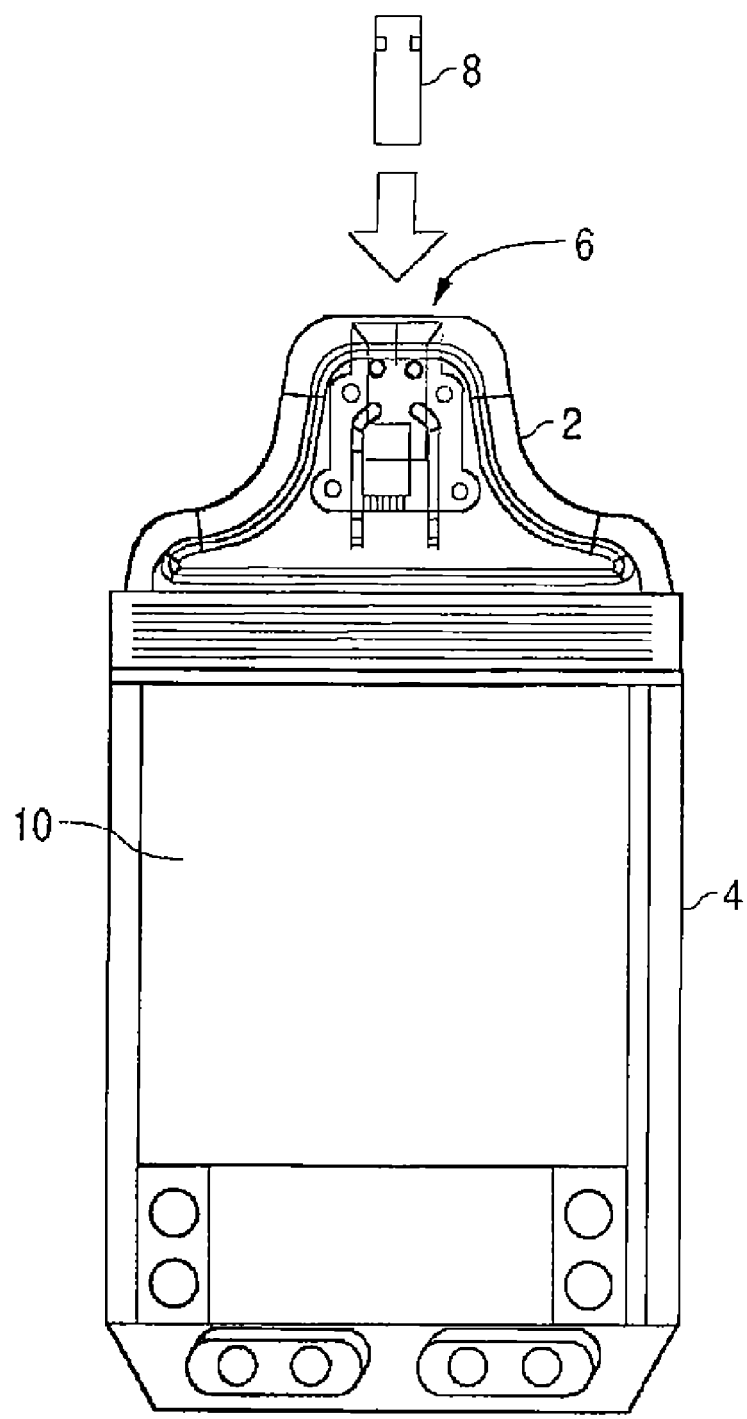
FIG. 1 schematically shows a plan view of an integrated glucose measurement module and hand-held processing device, such as a personal digital assistant or PDA, or mobile phone, integrated phone and PDA, or other wireless device, according to a preferred embodiment.

What follows is a cite list of references each of which is, in addition to the background, the invention summary, the abstract and the claims, hereby incorporated by reference into the detailed description of the preferred embodiments below, as disclosing alternative embodiments of elements or features of the preferred embodiments not otherwise set forth in detail below. A single one or a combination of two or more of these references may be consulted to obtain a variation of the preferred embodiments described in the detailed description below. Further patent, patent application and non-patent references are cited in the written description and are also incorporated by reference into the preferred embodiment with the same effect as just described with respect to the following references:

U.S. patent application Ser. Nos. 09/413,565, 60/300,011 and 60/280,905, which are assigned to the same assignee as the present application;

Published U.S. application Ser. Nos. 2002029058, 2002025469, 2002008038, 2001054319, and 2001017269, which are also assigned to the same assignee as the present application;

U.S. Pat. Nos. 5,307,263, 5,601,435, 5,899,855, 5,974,124, 6,153,062, 6,330,426, 6,334,778, D427,312, D439,242, D426,638, D424,6966,338,790, 6,329,161, D450,854, 6,299,757, 6,294,281, 6,281,006, 6,251,260, 6,175,752, 6,120,676, 6,103,033; and GB 1579690, GB 2225637, GB 2194892, GB 2073891, GB 2154003, and GB 2204408; and EP 0504835, EP 0799896, EP 0800082, EP 0880936, EP 0048090, EP 0078636, EP 0096288, EP 0125139, EP 0136362, EP 0170375, EP 0080304, EP 0184909, EP 0206218, EP 0230472, EP 0241309, EP 0245073, EP 0278647, EP 0286084, EP 0359831, EP 0368209, EP 0390390, EP 0400918, EP 0453283, EP 0470290, EP 0255291, EP 0127958, EP 0781406 and EP 1147739 A2; and PCT applications No. WO 86/00513, WO 89/02246, WO 90/00367, WO 95/06240, WO 96/07907, WO 96/07908, WO 96/07893, WO 97/20207, WO 97/41421, WO 97/46868, WO 98/09167, WO 98/24366, WO 98/52045, WO 99/05966, WO 99/32883, WO99/467582, WO 00/13580, WO 00/20626, WO 00/33065, WO 00/78210, WO 01/24038, WO 01/52727, WO 01/33216, WO 01/57238, WO 01/57239, WO 01/67009, WO 85/05119, WO 89/08713, WO 90/05300, WO 91/04704, WO 92/13271, WO 94/20602, WO 94/27140, WO 95/02817, WO 97/00441, WO 97/18464, WO 97/19344, WO 97/42882, WO 97/42883, WO 97/42886, WO 97/42888, WO 97/43962, WO 99/08106, WO 01/88524, WO 01/36430, WO 01/36660, WO 00/78992 and WO 99/30152; and Schrezenmeir, et al., Computer Assisted Insulin Dosage AdjustmentPerspectives for Diabetes Control, Hormone and metabolic Research, Supplement Series Vol. No. 24, pp. 116-123 Theme Medical Publishers (1990);

A. Michael Albisser, Intelligent Instrumentation in Diabetic Management, Vol. 17, Issue 1, pp. 1-24 (1989);

J. Stuart Soeldner, Treatment of Diabetes Millitus by Devices, the American journal of Medicine, Vol. 70, 183-194 Oanuary 1981);

New Computer Uses Can Improve Diabetics' Lot, The American Journal of Pharmacy, Vol. 70, pp. 144, 146 (February 1989);

Hiroyuki Horio, Clinical Telecommunication Network System for Home Monitoring, Med. & Biol. Eng. & Comput., 32, 227-230 (March 1994);

A. S. Douglas et al., Hand-Held Glucose Monitor and Recorder, Proceedings of the Annual International Conference of the IEEE Engineering in Medicine and Biology Society, New Orleans, 747-748 (Nov. 4-7, 1988);

User's Guide, Accu-Chek Compass Diabetes Care Software, Roche Diagnostics, pp. 1-93 (2000);

Laughton E. Miles, A Portable Microcomputer for Long-Term Physiological Monitoring in the Home and Work Environment, pp. 47-57, Raven Press, eds. Laughton E. Miles and Rogerj. Broughton (1990);

P. G. Fabietti et al., Wearable System for Acquisition, Processing and Storage of the Signal from Amperometric Glucose Sensors, International Journal of Artificial Organs, Vol. 14, No. 3, pp. 175-178 (1991);

Heller, A., "Amperometric biosensors based on three-dimensional hydrogelforming epoxy networks," Sensors and Actuators B, 13-14:180-183 (1993);

Heller, A., "Electrical Connection of Enzyme Redox Centers to Electrodes," J. Phys. Chem., 96(9):3579-3587 (1992); and Heller, A., "Electrical Wiring of Redox Enzymes," Acc. Chem. Res., 23(5):129134(1990).

DETAILED DESCRIPTION OF THE INVENTION

FIG. 1 schematically shows a perspective view of an integrated glucose measurement module 2 and a hand-held processing device 4, such as preferably a personal digital assistant (PDA) 4 or a mobile phone or combined PDA/phone or other wireless device with a processor as may be understood by those skilled in the art. Hereinafter when the term PDA is used it is meant to refer to any of these or other hand-held processing devices, any of which may also be operated using hands-free accessories and/or equipment. The glucose measurement module 2 (hereinafter "module 2") is shown in FIG. 1 mechanically attached to the PDA 4. The module 2 is in this way physically mounted to and integrated with the PDA 4. The module 2 is also electrically connected to the PDA 4 when mounted into the PDA 4. In addition, the module 2 is software interfaced with the PDA 4 when mounted into the PDA 4. The module 2 shown in FIG. 1 preferably does not have a display, since the display of the PDA 4 may be used for displaying information. The PDA 4 may be replaced by another processing device having a display such as a mobile phone having a connector for attaching the module 2.

The module is shown having a slot 6 for insertion of an in vitro test strip 8. Some details may be found at U.S. patent application Ser. No. 09/413,565, which is assigned to the same assignee as the present application and is hereby incorporated by reference. When the test strip 8 is inserted into the slot 6, preferably blood such as whole blood, plasma and/or serum, and alternatively another body fluid such as interstitial fluid, sweat, urine, tears, saliva, dermal fluid, spinal fluid, etc., is applied to the strip 8 and the module 2 measures the glucose level of the body fluid applied to the strip 8. Hereinafter, whenever blood or body fluid is referred to for being applied to the strip 8, it is meant to include whatever body and/or biological fluid that may be applied to strip 8 for testing. The glucose level data automatically transfers to the PDA 4 (the data transfer mechanism is described in more detail below with reference to FIGS. 2-5), and the glucose level in the blood tested is displayed on the display 10 of the PDA 4, or transmitted through a speaker or otherwise to a user of the device shown in FIG. 1.

The PDA 4 is configured to HotSync with a PC for transmitting data to a PC. The PDA 4 may also transmit data by wireless RF and/or IR connection to a remote or host client or server computer. The PDA 4 also preferably has internet connectability or is otherwise configured for logging into a network for transmitting and receiving data from the network.

Figure 2:
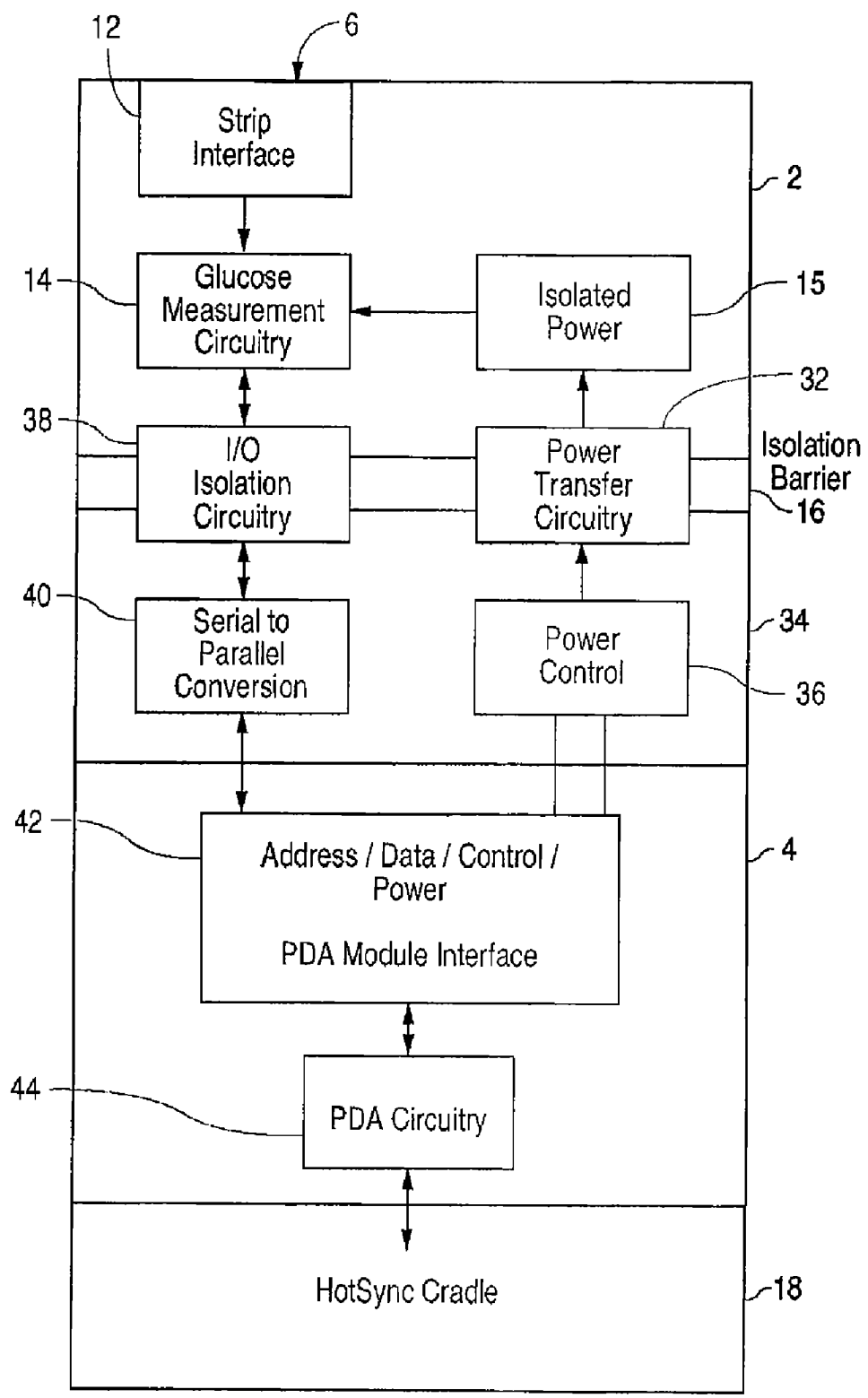
FIG. 2 shows a block diagram of electrical modules of the integrated glucose measurement module and PDA of FIG. 1.

FIG. 2 shows a block diagram of electrical modules of the integrated glucose measurement module 2 and PDA 4 of FIG. 1. At the point of the in vitro test strip slot 6 at the top of FIG. 2 is a strip interface 12 including circuitry for connecting to an in vitro test strip for passing a current through blood applied to the strip. Glucose measurement circuitry 14 is shown connected to the strip interface 12 for measuring one or more parameters indicative of a blood glucose level of the blood applied to the strip. An isolated power module 15 provides power to the glucose measurement circuitry 14 and strip interface 12 and ultimately to the test strip.

An isolation barrier 16 is shown for isolating the power at the module from the power at the PDA 4. The isolation barrier 16 is provided to protect the user from having a high current pass through his or her body when the PDA 4 is in a HotSync cradle 18 and thus is connected to AC power. Since an electrically conductive part of the integrated measurement module 2/PDA 4 system (i.e., a strip) contacts the patient, the system may be considered to have a "patient applied part" and would be bound to comply with applicable standards (AAMI ES1, IEC60601-1-2, etc) for isolated patient connections. These standards contain requirements for a maximum amount of current that can flow in either direction between the patient and an AC power line or ground with either the module 2 or the patient in contact with 1 10% of line voltage.

When the glucose measurement module 2 is inserted into the PDA 4 and the PDA 4 is connected to it's HotSync cradle 18 as shown in FIG. 2, AC ground is connected to the module 2. This connection is made because the ground connection of the HotSync cradle 18 to the PDA 4 is connected to ground at the computer to which the HotSync cradle is connected, which is in turn connected to earth ground at the AC outlet. If AC voltage is applied to the strip connector 12, a large amount of current would flow to AC ground through the module 2, PDA 4, HotSync 18, and/or computer circuitry.

Figure 3A:
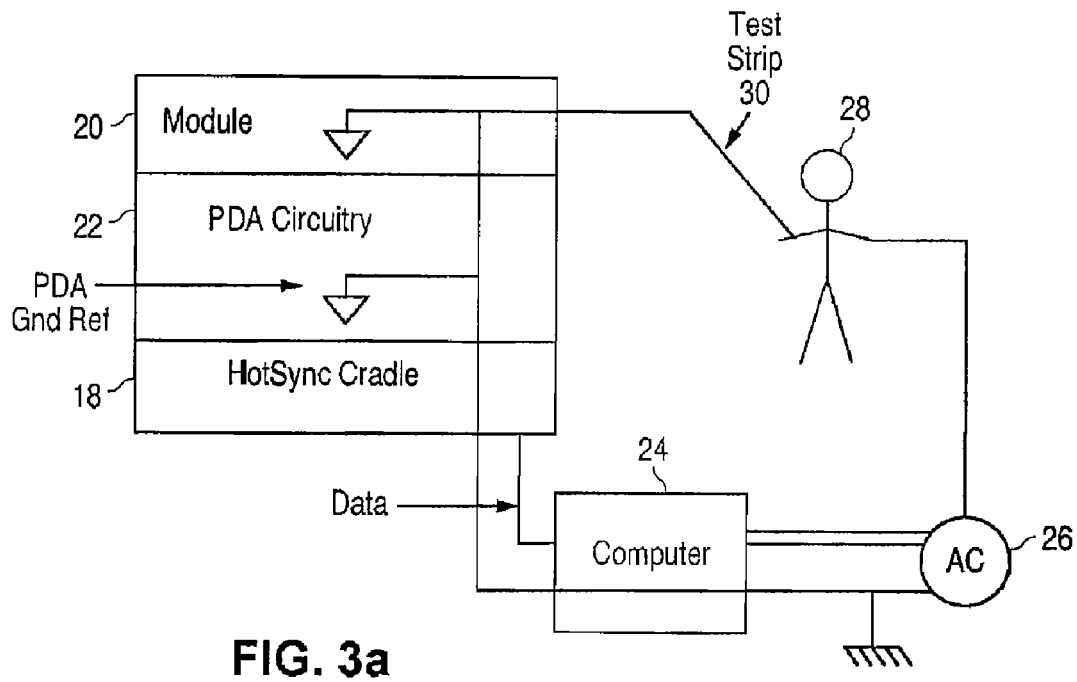
FIGS. 3a and 3b schematically illustrate an advantageous electrical isolation barrier feature of an integrated module and PDA according to a preferred embodiment.

Referring to FIG. 3a, a module 20 connected to PDA circuitry 22 and not having the electrical isolation barrier 16 of FIG. 2 is illustrated. A patient 28 is shown contacting a test strip 30, e.g., for applying blood to the strip or for inserting the strip into the module 20. The patient 28 is also contacting AC power 26 which also powers a computer 24. The computer 24 is shown communicating with the PDA 22 through the HotSync cradle 18. AC ground is shown connected to the computer 24, the Hotsync cradle 18, the PDA circuitry 22, and the module 20. If the user 28 became in contact with the test strip 30 and inadvertently came in contact with any earth referenced potential, large currents would flow through the user 28, and back to earth ground via this path. Conversely, if the module 20 or test strip 30 were to be inadvertently raised to a high potential reference to earth ground, again large currents would flow through the user 28. The risk in each case is electrocution of the user 28 and the standards consider having the user 28 in contact with significant potentials a viable scenario. Should even very small currents flow across the heart, e.g., there is significant risk of causing fibrillation.

Figure 3B:
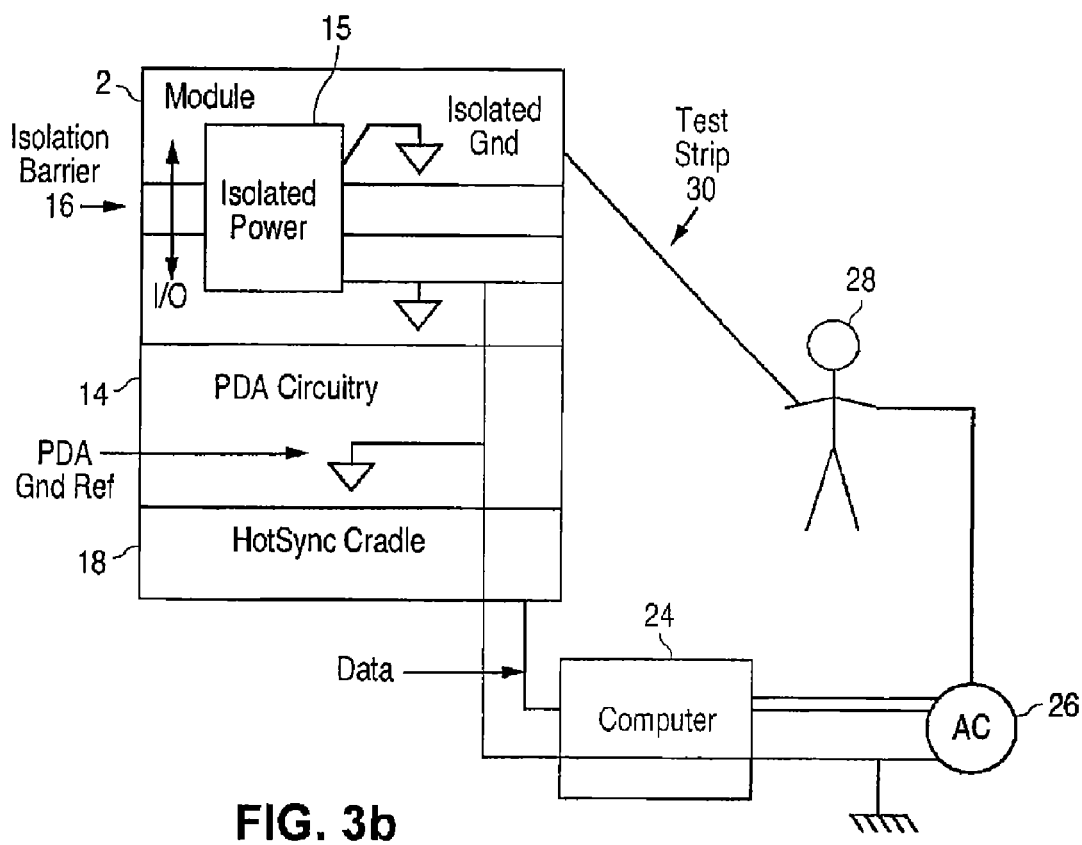

In order to prevent this potentially dangerous situation, electrical connections which come into contact with the user 28 at the strip connector 30 are advantageously isolated from earth ground or AC in accord with a preferred embodiment. FIG. 3b illustrates the scenario described above with respect to FIG. 3a except that the module 2 includes the isolation barrier 16 referred to above with reference to FIG. 2. The user 28 who is shown in FIG. 3b in contact with AC power 26 to the computer 24 is also contacting the strip 30 which is connected to the module 2. In contrast with the scenario illustrated by FIG. 3a, the strip 30 is not connected to AC ground, and thus no currents pass through the user 28.

This isolation barrier 16 is preferably created via a physical or otherwise insulating gap in the circuitry on the PC board or the module 20. A preferred dimension of this gap is around 4 mm and is generally dictated by electrical safety standards.

Referring back now to FIG. 2, the glucose measurement circuitry 14 and strip interface 12 are shown on the isolated side of the barrier 16. Power for this isolated circuitry is created by power transfer circuitry 32, which is a transformer coupled, switching power supply according to a preferred embodiment. The transformer 32 bridges the isolation barrier 16 and transfers isolated power 15 to the isolated side of the barrier 16 from the PDA-to-module interface connector 34. For sufficiently low power consumption requirements, a capacitively-coupled supply would be a viable alternative power transfer circuitry 15. Switching control circuitry 36 is on the PDA (ground referenced) side of the isolation barrier 16.

A glucose value is calculated by circuitry 14 on the isolated side of the barrier 16. The glucose value, status, and errors are communicated across the isolation barrier 16 preferably via a bidirectional serial interface 38. Control commands may be preferably received from the PDA 4 via this same interface 38. Serial communication lines of the serial interface 38 bridge the isolation barrier 16 preferably via optoisolators (not shown, but see FIG. 5 and discussion below). Serial information is converted to parallel by serial to parallel conversion circuitry 40 within the module 2 on the PDA side of the barrier 16, so that the module 2 can communicate with the PDA 4. The PDA interface 42 at the module connector 34 is parallel access directly to a PDA data/address bus of PDA circuitry 44. This interface 42 includes control lines as well as power connections.

As an alternative to providing an electrical isolation barrier between module 2 and PDA 4, features can be incorporated into module 2 that prevent it from being used at the same time that PDA 4 is connected to a HotSync cradle or cable, thereby eliminating the risk of passing high levels of electric current through the cradle or cable to or from the patient. This can be accomplished by providing an extended portion of the housing of module 2 that extends down along PDA 4 to interfere with the attachment of a cradle and/or cable to PDA 4 when module 2 is first attached thereto, or prevent the attachment of module 2 when a cradle or cable is already attached to PDA 4.

Figure 4:
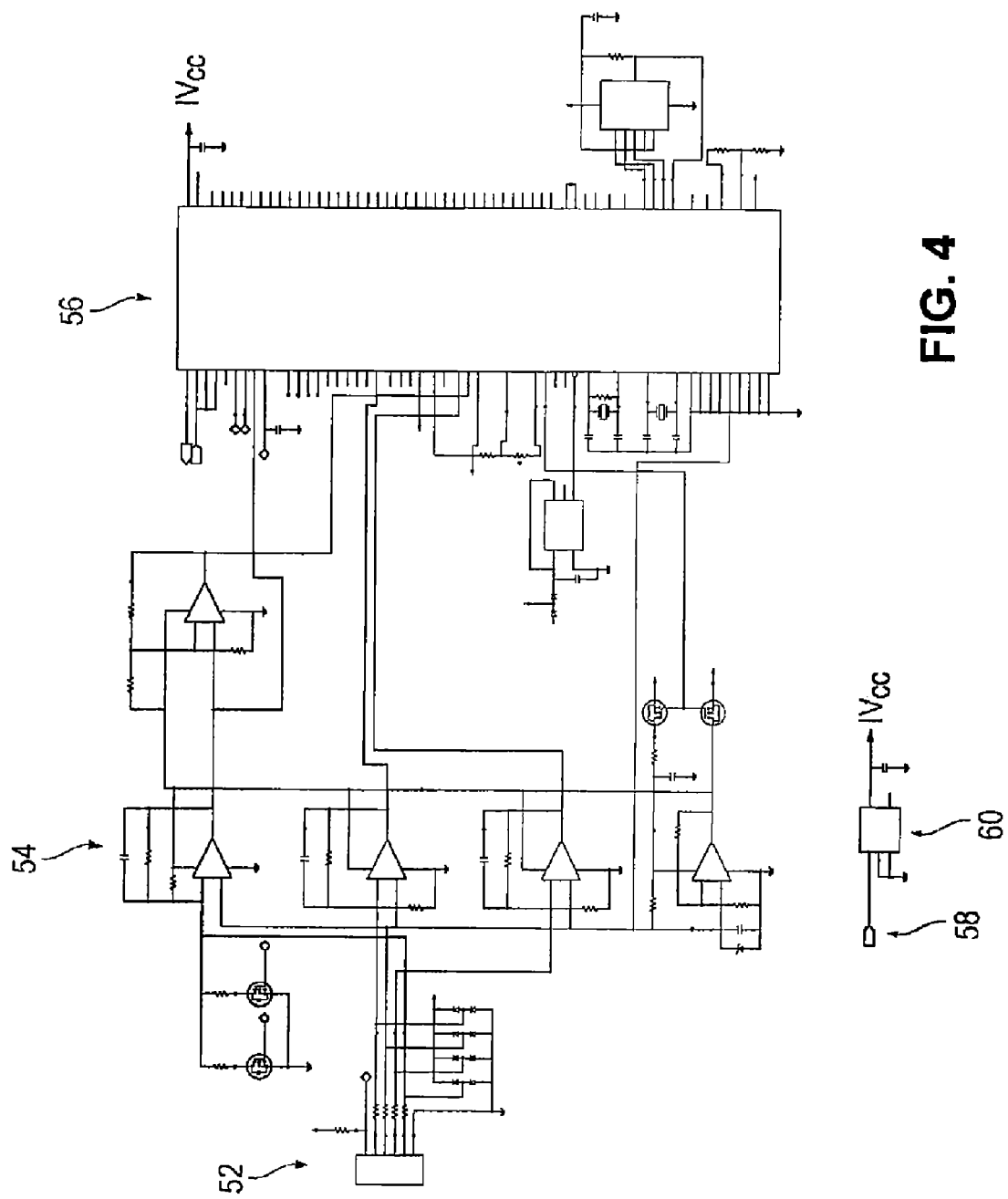
FIG. 4 shows an electrical circuitry schematic of a glucose measurement module for integrating with a PDA according to a preferred embodiment.

FIG. 4 shows an electrical circuitry schematic of a glucose measurement module for integrating with a PDA according to a preferred embodiment. The electrical schematic shown in FIG. 4 shows a strip connector 52 for making electrical connection to a strip 8 inserted into the slot 6 of the module 2 of FIG. 1. Analog front end signal acquisition circuitry 54 is shown for acquiring signals indicative of a blood glucose level in blood applied to the strip 8 (FIG. 1). A microprocessor 56 is shown for controlling the module 4. The microprocessor 56 receives isolated power (see element 15 of FIG. 2) as isolated voltage IVcc from an unregulated voltage at point 58 of the schematic of FIG. 4 appearing on the isolated side of the barrier (which is the barrier 16 of FIG. 2), and regulated through regulator 60.

Figure 5:
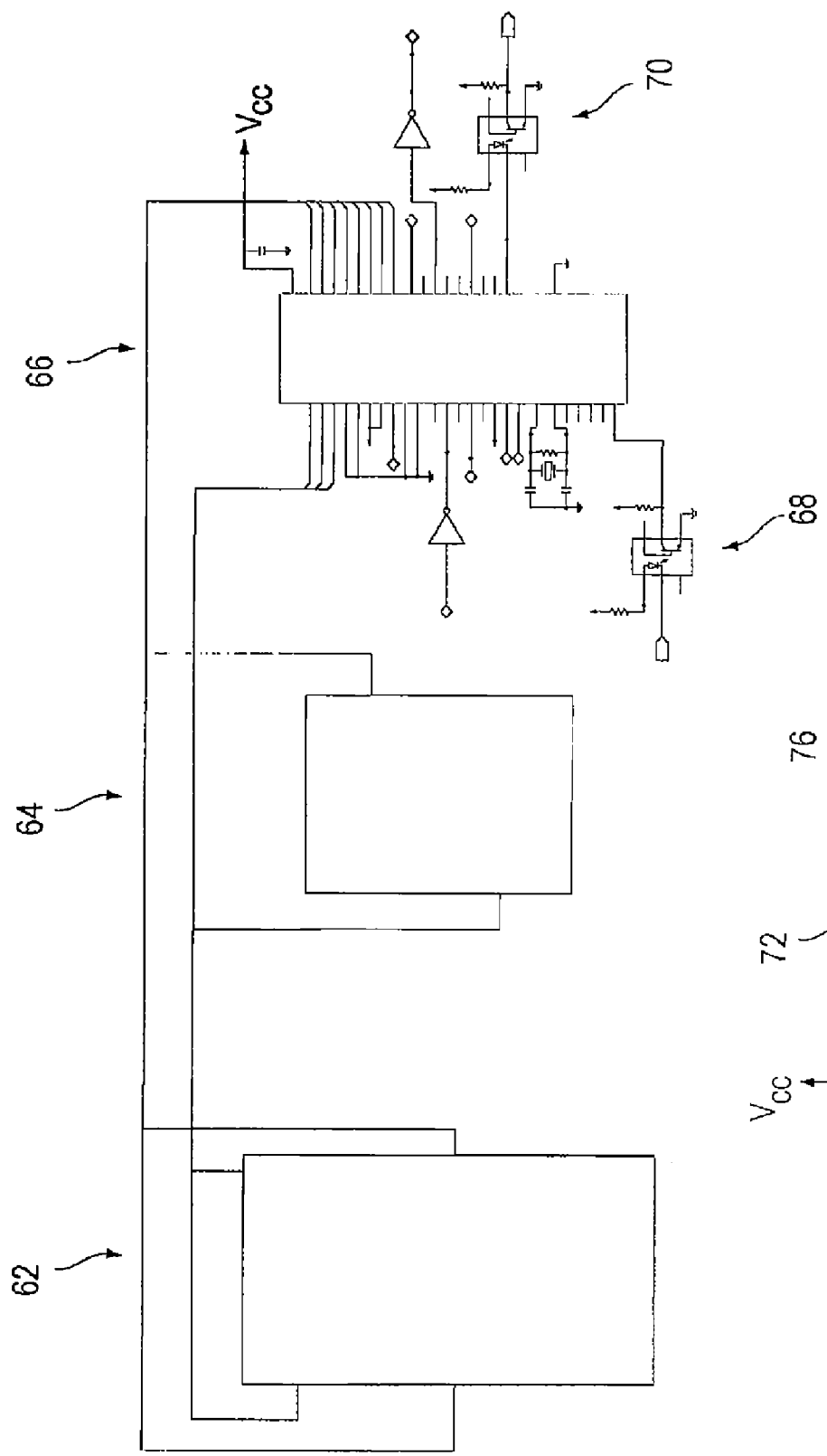
FIG. 5 shows an electrical circuitry schematic of a PDA for integrating with a glucose measurement module according to a preferred embodiment.

FIG. 5 shows an electrical circuitry schematic of a PDA for integrating with a glucose measurement module according to a preferred embodiment. A connector 62 for mounting the module 2 with the PDA 4 as shown in FIG. 1 is shown next to a memory 64 for storing digital data. At the right in FIG. 5 is a universal asynchronous receiver/transmitter or UART 66. The UART is on the non-isolated side of the barrier 16 of FIG. 2. The UARTs perform the serial to parallel conversion of element 40 of FIG. 2.

Data is transmitted serially from the glucose module 2 to the UART 66 (or converter 40 of the module 2 of FIG. 2) through optoisolator 68. Data is transmitted serially from the UART 66 to the isolated side of the barrier 16 of FIG. 2 through the optoisolator 70. Data may alternatively be transferred across the barrier 16 in parallel. Additional optoisolator components would be used for parallel data transfer compared with serial transfer. Serial transfer is preferred and allows the module 2 to be smaller, more economical to manufacture and more power efficient than if parallel transfer and additional optoisolators are used.

Power is transferred from the PDA 4 through the transformer (corresponding to the power transfer circuitry 32 of FIG. 2). The transformer is preferably a 1:1 transformer, and may be a step-down or step-up transformer of a desired ratio. Through the transformer, power as voltage Vcc is transferred from the non-isolated side of the barrier 16 to the isolated side as isolated power 76. The power may be around 3.3 Volts according to a preferred embodiment.

Figure 6A:
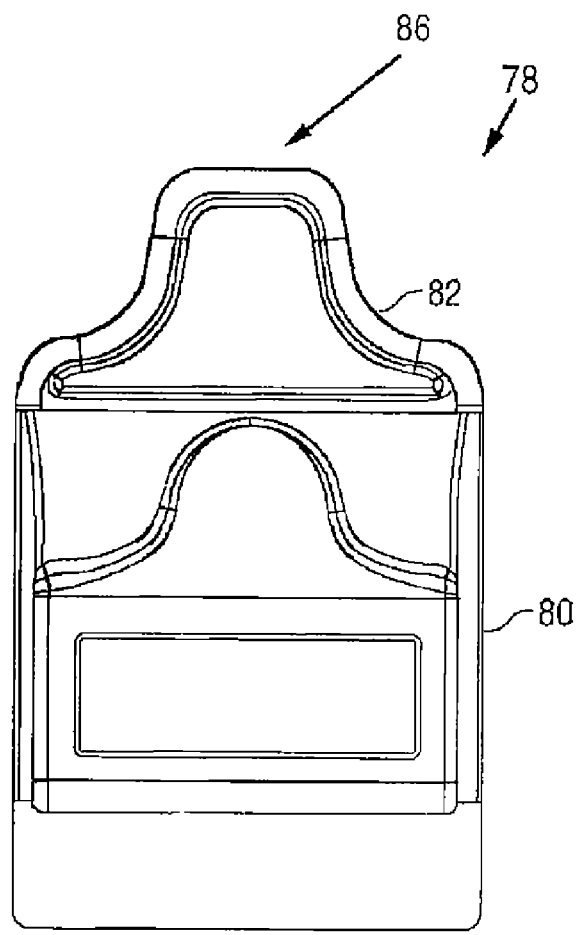
FIG. 6a schematically shows a bottom plan view of a glucose measurement module for integrating with a PDA according to a preferred embodiment.

FIG. 6a schematically shows a plan view of a glucose measurement module 78 for integrating with a PDA (not shown, but see FIGS. 7a-7b) according to a preferred embodiment. The module 78 includes a mounting portion 80 and a specially shaped extension portion 82. When the module 78 is inserted into a PDA and is mechanically and electrically attached to the PDA and configured to transfer data to/from the PDA, the mounting portion 80 is within the PDA and the extension portion 82 protrudes outside of the PDA.

The module 78 (corresponding to the module 2 of FIG. 2) is about 54 mm wide at the mounting portion 80 which plugs into the PDA 4 and scales down to around 23 mm at the end 86 of the extension portion 82 where the strip 8 of FIG. 1 is inserted. The extension portion 82 itself measures about 54 mm in width at the other end where the mounting portion 80 begins and the extension portion 82 is preferably about 28 mm long from the mounting portion 80 to the strip insertion end 86. The shoulder from which the extension portion 82 narrows most drastically in about 8.5 mm in extent o the approximately 28 mm extent of the extension portion 82. The curvature from the shoulder is about 0.5 rho, which changes direction at a curvature of about 0.5 rho and which changes direction again at a curvature of about 0.6 rho to the strip insertion end 86. As the shoulder flattens out, it makes an angle of about 100° with the elongated direction of the module 78 from the strip end 86, or 80° looking at it from the direction of the mounting portion 80, which angle can be varied somewhat while maintaining the shoulder and also the smoothness of the rounding of the extension portion 82. The extension portion 82 is shown symmetric, but may have an arbitrary curvature on one side the module 78 will be used by resting the extension portion on only the side with rounded features as just described, i.e., it is preferred there are no sharp corners on at least one side of the extension portion 82, and it is more particularly preferred that no sharp corners exist anywhere on the extension portion 82, nor even on the mounting portion 80.

Figure 6B:
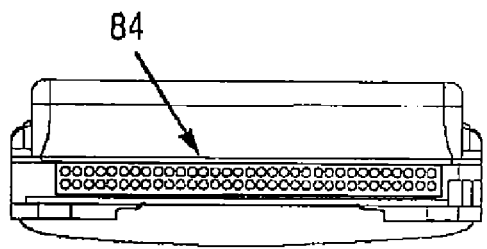

The mounting portion 80 connects electrically and for data transfer to the PDA by preferably a 68 pin electrical connector 84 as shown in FIG. 6b for connecting to a complementary 68 pin male connector of the PDA, wherein the male and female configuration may be reversed or mixed. The thickness of the module 78 is indicated as preferably around 19 mm. FIG. 6b schematically shows a rear view of the glucose module of FIG. 6a. Although not shown, the module 78 attaches mechanically in place in the PDA receptacle by a pair of mechanical latches preferably on opposing sides, e.g., the left and right side in FIG. 6a, of the PDA receptacle.

The extension portion 82 is particularly ergonometrically and/or arthopometrically configured so that a patient may insert a strip into a strip insertion slot (corresponding to slot 6 of FIG. 1) at the end 86 of the extension portion 82, and so that the patient can contact the strip with a drop of blood on the skin of the patient's body. The device is configured so that the patient may choose to use his or her arm, leg or any convenient anatomic location including the finger. This is advantageous because conventional systems often require application of blood to the strip at the finger.

A feature of the shape of the extension portion 82 is its protruding and/or telescoping trapezoidal profile. A utility design is provided at the extension portion 82 of the module 78 that promotes easy and efficient manipulation of the glucose strip on the blood drop whether if be on or off-finger or at an alternate site. The PDA module design incorporates a telescoping trapezoidal profile that allows ease of placement and inhibits the PDA body from encroaching or otherwise interfering with the placement, e.g., at a patient's arm. At the same time, the design is unobtrusive, streamlined and safe.

The telescopic and/or protruding trapezoidal profile of the module includes generous radii on each of the compound edges shown in FIG. 6a. The design allows easy and effective collection of a blood sample from any approved site on the body. The design allows for ease of positioning the module in the proximity of the blood drop and when actually placing the glucose strip on the blood drop. The preferred radii of curvature of each of the three bends on each side of the slot 86 of the extension portion 82 of FIG. 6a are drawn to scale. The curvatures are selected such that the PDA does not interfere with the blood application to the strip, e.g., from a patient's arm, leg or other approved off-finger location, and such that the shoulders of the extension portion 82 of the module 78 may rest gently on the patient's arm while the blood is applied, if the patient chooses, e.g., for support and/or stability. In addition, the design allows for a discreet and unobtrusive profile extending from the PDA. The design is compact and portable and preferably does not include cumbersome and potentially hazardous cables and extra attachments.

Figure 6C:
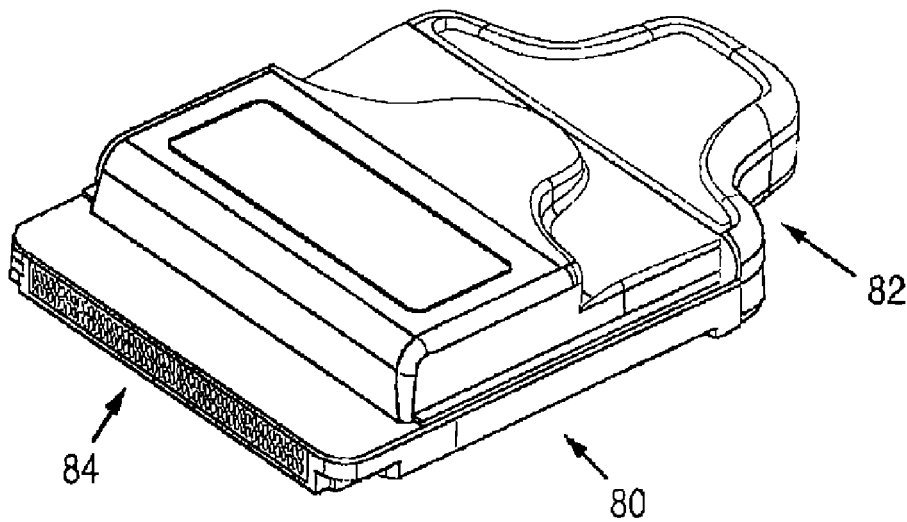
Figure 6D:
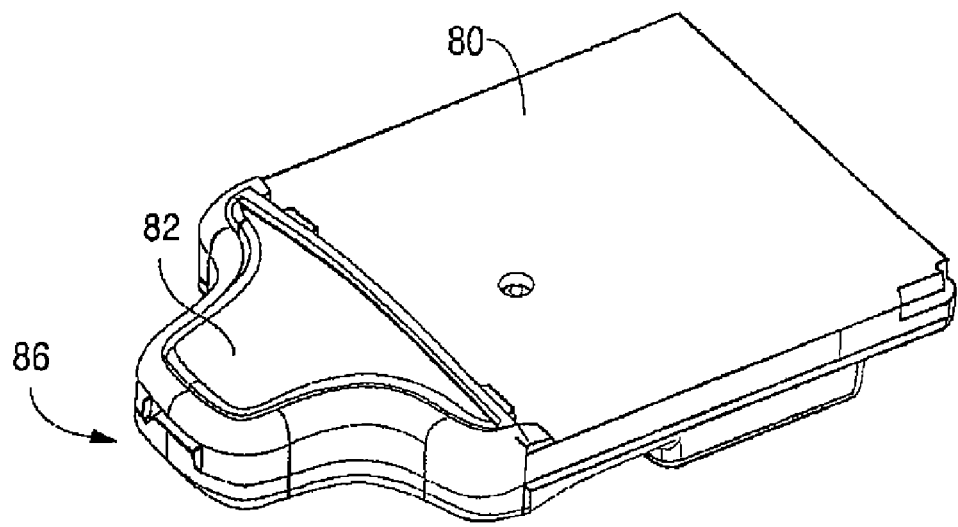
Figure 6E:
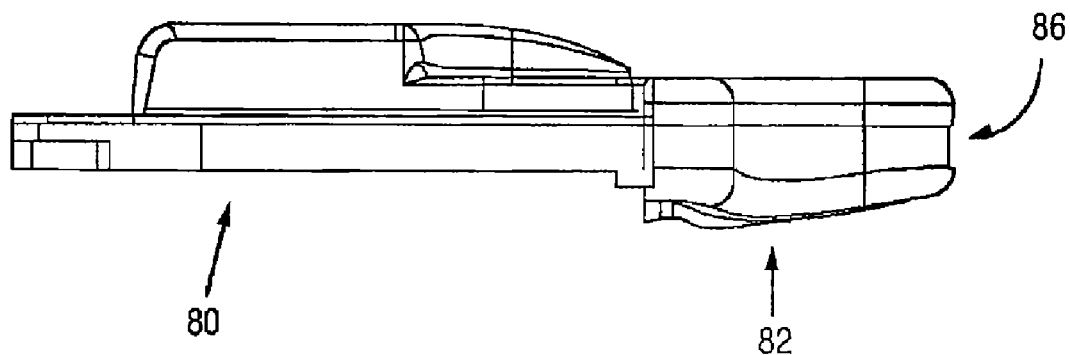
Figure 6F:
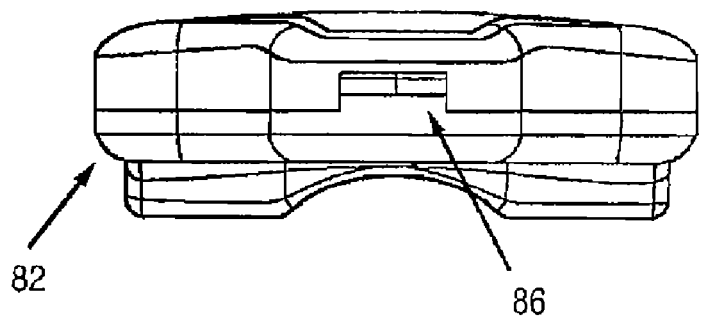

The extension 82 is preferably rounded in three dimensions or at least two dimensions, e.g., as illustrated by the various views of the preferred embodiment shown in FIGS. 6c-6f, and as mentioned, preferably has no sharp corners on at least one side which may be rested upon an arm or leg near an alternate site testing location, and for displaying information while testing on each arm for different tests such as on different days, the extension 82 is preferably rounded on both side and is particularly preferably symmetric as shown. FIG. 6c schematically shows a bottom perspective view of the glucose module 78 of FIG. 6a with extension portion 82, mounting portion 80 and pin connector 84. FIG. 6d schematically shows a top perspective view of the glucose module 78 of FIG. 6a with mounting portion 80, extension portion 82 and strip insertion end 86. FIG. 6e schematically shows a side view of the glucose module 78 of FIG. 6a, indicating a total length of about 85 mm, a thickness of about 14 mm at the extension portion 82 and a thickness of about 0.9 mm at the mounting portion 80, wherein the extension portion 82 and mounting portion 80 couple in a staggered fashion with each portion 80 and 82 having an edge which looks out somewhat over the other. FIG. 6f schematically shows a front view of the glucose module of FIG. 6a with the strip insertion portion 86 showing at the end of the extension portion 82. The corners are rounded with radius of curvature about 2.6 mm in the middle of the curve.

Figure 6I:
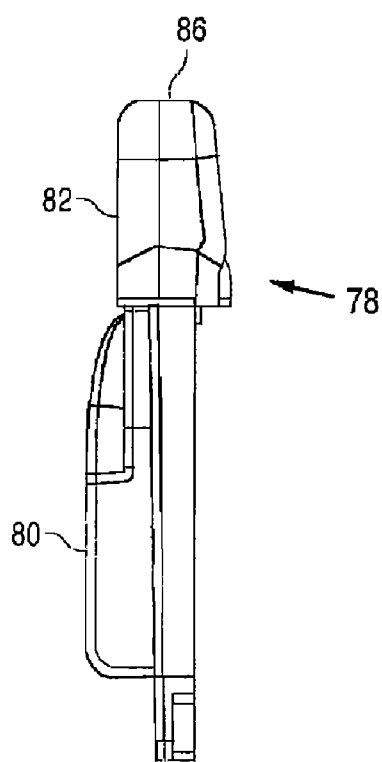
FIG. 6i schematically shows another rear view of the preferred glucose module with preferred dimensions shown in millimeters.
Figure 6I:
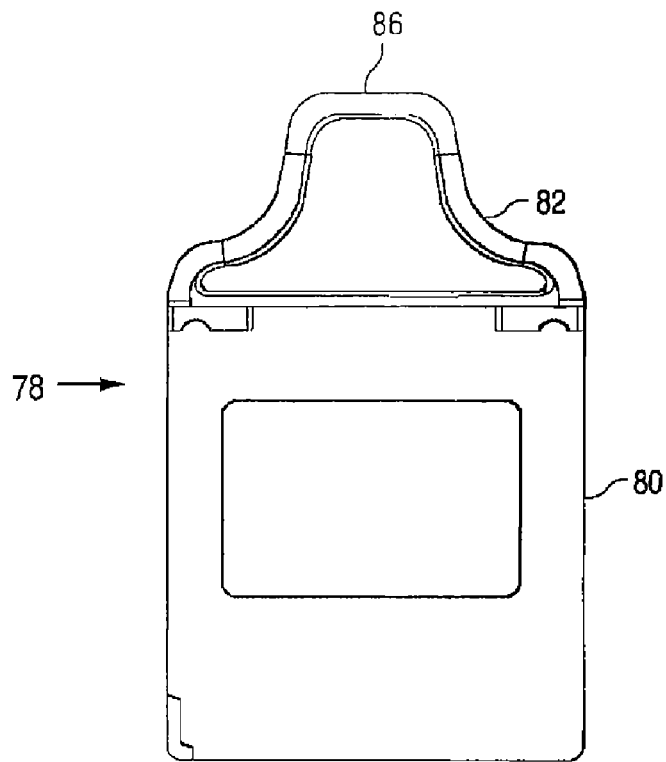
Figure 6I:
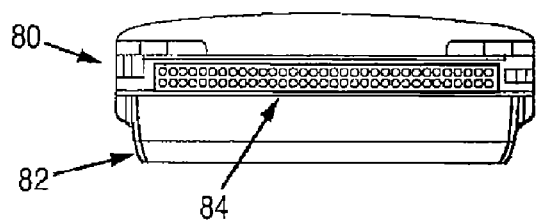

FIGS. 6g, 6h and 6i schematically show another side view, a top view and another rear view of the preferred glucose module with preferred dimensions shown in millimeters. Referring to FIG. 6g, the mounting portion 80 of the module 78 has a thickness of around 14.3 mm, which differs from the 0.9 mm thickness shown at FIG. 6e. The thickness, as well as the width and/or length, of the mounting portion 82 is preferably set to adapt to the dimensions of the receptacle of the hand-held processing device (e.g., PDA, mobile phone, combined PDA/phone, etc.) that the module 78 is to be connected, and these dimensions will vary depending on the device, and so no fixed numeric dimensions are necessarily universally preferred. The rounding of the strip insertion end 86 of the extension portion 82 is shown as having minimum radii of curvature of 9 mm on the bottom side and 2.5 mm on the top side. Referring to FIG. 6h, the rounding from the shoulder of the extension portion has a minimum radius of curvature around 12 mm, while the rounding which is opposite in direction as the rounding from the shoulder has a curvature radius of about 33 mm and that final rounding near the strip insertion end 86 is about 22 mm at minimum. Referring to FIG. 6i, a thickness of around 19.5 mm is shown for the rear view, which shows the pin connector 84, including the thickness of the mounting portion 80 added with the staggered overlooking portion of the extension portion 82, as briefly described above, i.e., so that the staggered overlook portion of the extension portion 82 is about 5 mm.

As shown in FIGS. 6a-6i, the extension portion 82 is rounded away from each side of the slot 86 in two orthogonal directions, and rounds from the slot 86 toward the mounting portion 80, corresponding to a third direction in which the extension portion 82 of the module 78 is rounded. This advantageous design prevents potential hazards such as pinching, lacerations, cuts or skin abrasions, during normal use and handling.

The module 78 serves as a housing for the strip connector, PC board and the opto-isolation components, while not appearing bulky or obtrusive. As mentioned above, the module 78 does not include a display such as a LCD screen because the PDA display may be used as an advantageous PDA accessory for displaying blood glucose levels without delay due to the integrated design of the module 78 with the PDA (see FIG. 1). This contributes to the compactness feature of the design, enabling the module 78 to entend less than two inches beyond the end of the PDA, and as shown in FIG. 6a, less than 1.5 inches and even below 1.2 inches. The module 78 at the extension portion 82 is around or less than 0.25 inches thicker than the PDA. The module 78 weighs less than two ounces and the preferred embodiment shown is around 1.1 ounces, while the design may be configured at less than one ounce. In contrast, if a display such as an LCD were included in the module 78, the module 78 would likely be 50-60% longer, 0.25 inches thicker and be at least two ounces. The preferred module 78 thus does not have a display, and is thus smaller and lighter than if it did have a display, while the integrated module-PDA system has full display capability. Obtaining power to run module 78 from the PDA rather than from an internal power source also contributes to the light, compact arrangement shown.

The module 78 shown and described with respect to FIGS. 6a and 6b including the telescoped, trapezoidal-shaped design has fully-radiused shoulders in an advantageous profile. Some preferred radii and compound angle values are shown in FIG. 6a. From the slot 86, the design rounds toward the PDA at a preferred radius of curvature of 0.6 rho, then rounds in the opposite direction away from the slot 86 at a preferred 0.5 rho and then reverses its curvature again toward the PDA at a preferred 0.5 rho.

The module 78 advantageously mates with a PDA device and forms a single, hand-held unit for glucose measuring and data management. The mechanical design shown in FIGS. 6a-6f allows measurements to be taken that suppress problems that might otherwise present themselves such as interference by the bulky PDA in the blood application process, improper strip placement and positioning, potential for injury, and obtrusiveness. The glucose monitoring strip may be positioned to apply the blood drop, while being attached to the module 78 which is itself mounted into the PDA. The sheer size of the PDA in relation to the module 78 does not inhibit the application process due to the design of the extension portion 82 such that the PDA body does not interfere with or become a hindrance to placement. The shape the profile of the module actually conforms to the shape of a body part such as an arm to which it rested, without presenting itself with an "armsliding" problem, as the user positions the module 78 in close proximity to the blood drop. The rounded shape, generous radii and material selection reduce potential hazards to the user, in terms of cuts, lacerations or skin abrasions.

Alternative designs would provide for a more pointed profile to the module 78 to presumably provide easier access to the glucose strip or the module 78 may be alternatively connected through a strip connector and a flexible cable to allow flexibility of placement, independent of the PDA body. These alternative designs are not preferred, however, as the size of the pointed profile may be limited by the size of the strip connector and would likely not allow the user to effectively position the strip due to a lack of plastic real estate. Additionally, a flexible cable, although affording flexibility of placement, would be cumbersome and visibly obtrusive. The preferred design thus has the slightly wider tip such as shown in FIG. 6a and no cumbersome cable is used in the preferred embodiment which includes the module 78 directly mechanically coupled with the PDA.

The module 78 and particularly the extension portion 82 are made of a low durometer material or thermoplastic elastomer facepad detail on both sides of the enclosure, to act as a gripping surface for module insertion and extraction, as well as afford the module a measure of shock absorption. The material may preferably be a PC-ABS alloy or other non-filled plastic resin.

Figure 7A:
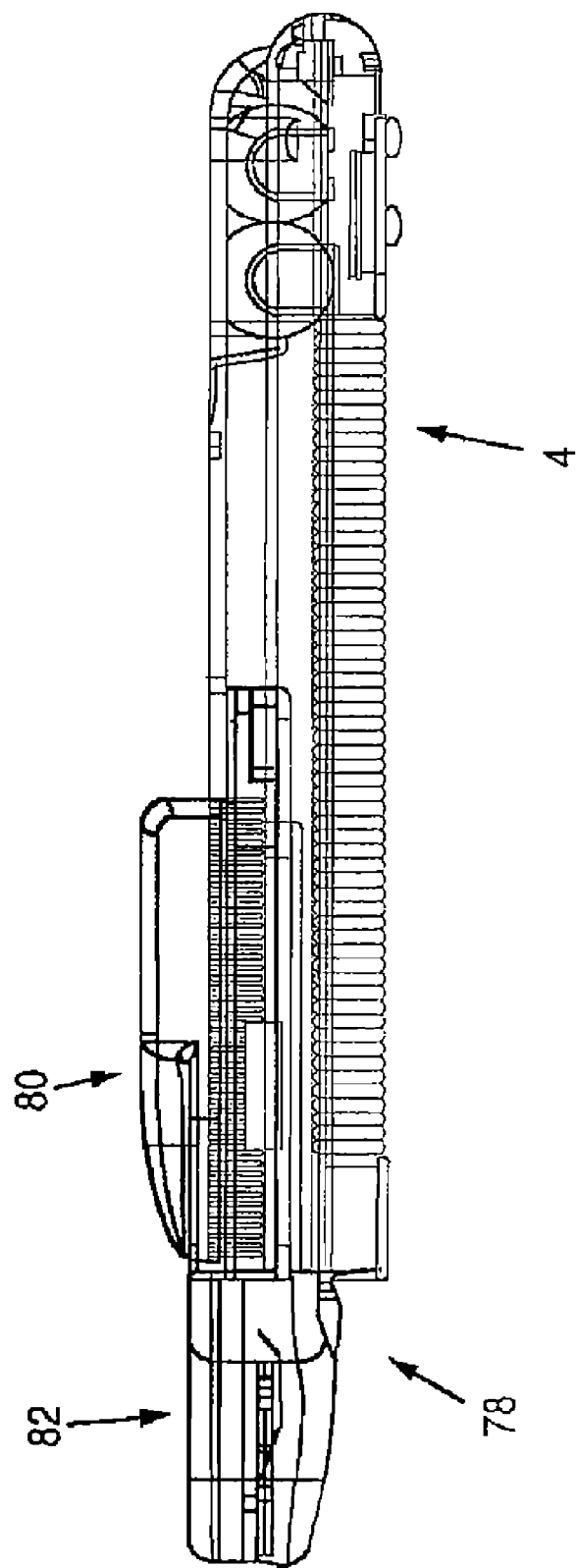
FIG. 7a schematically shows a side view of the measurement module of FIG. 6a integrated with a PDA according to a preferred embodiment.
Figure 7B:
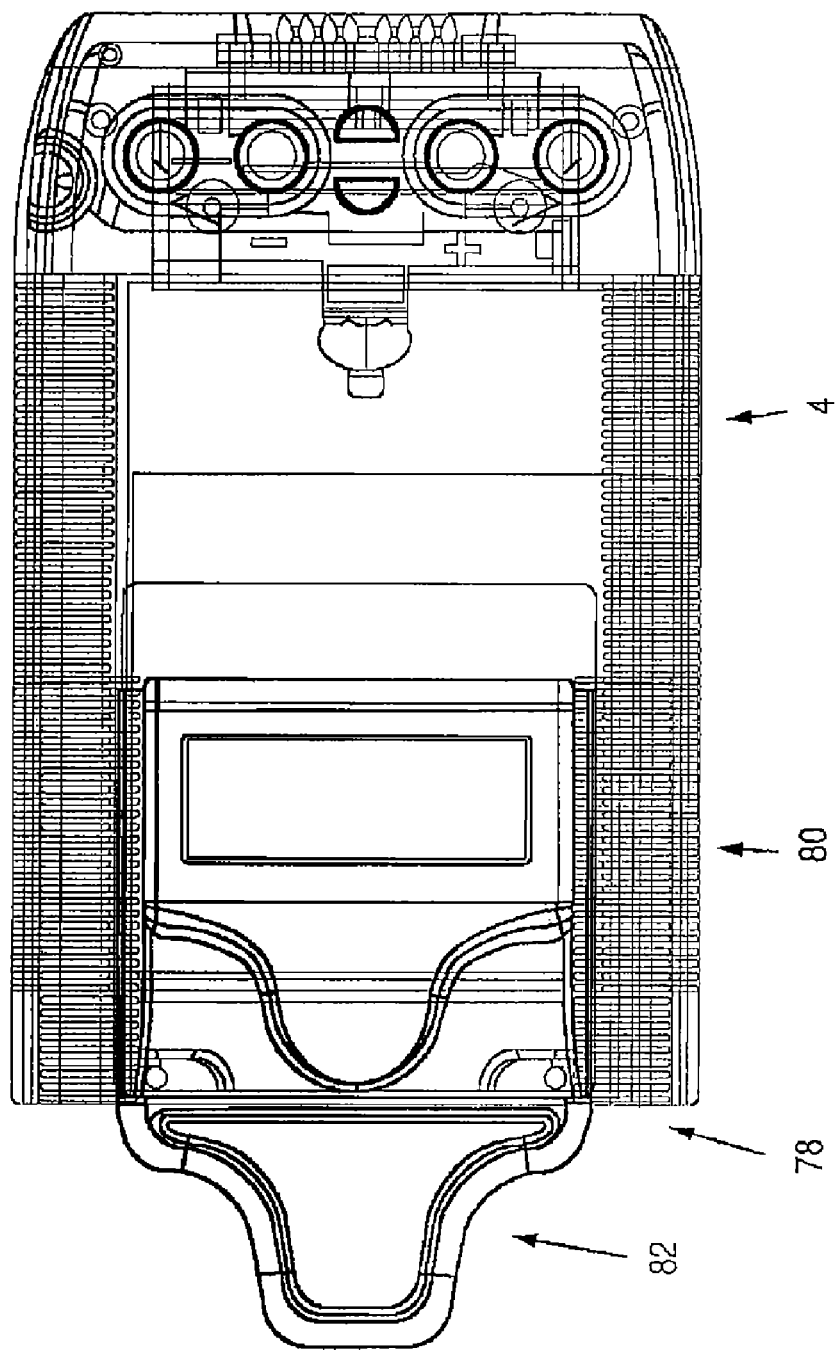

FIG. 7a schematically shows a side view of the measurement module 78 of FIG. 6a integrated with a PDA 4 according to a preferred embodiment. An indication of an staggered overlook portion of the extension portion 82 being 6.25 mm as opposed to the 5 mm shown about, again indicates that the dimensions of the module 78 can be varied to meet the specifications of the particular hand-held device 4 being used. The mounting portion 80 is shown inserted into the PDA 4 while the extension portion 82 is shown protruding from the PDA 4. FIG. 7b schematically shows a plan view of the integrated measurement module 78, with mounting portion 80 and extension portion 82, and PDA 4 of FIG. 7a. As shown, the extension portion 82, with length of about 28 mm, protrudes from the PDA 4 while the mounting portion 80 of the glucose measurement module 78, with overall length of about 73 mm, is inserted within the receptacle of the PDA 4 (or other hand-held processing device, see above).

Figure 8:
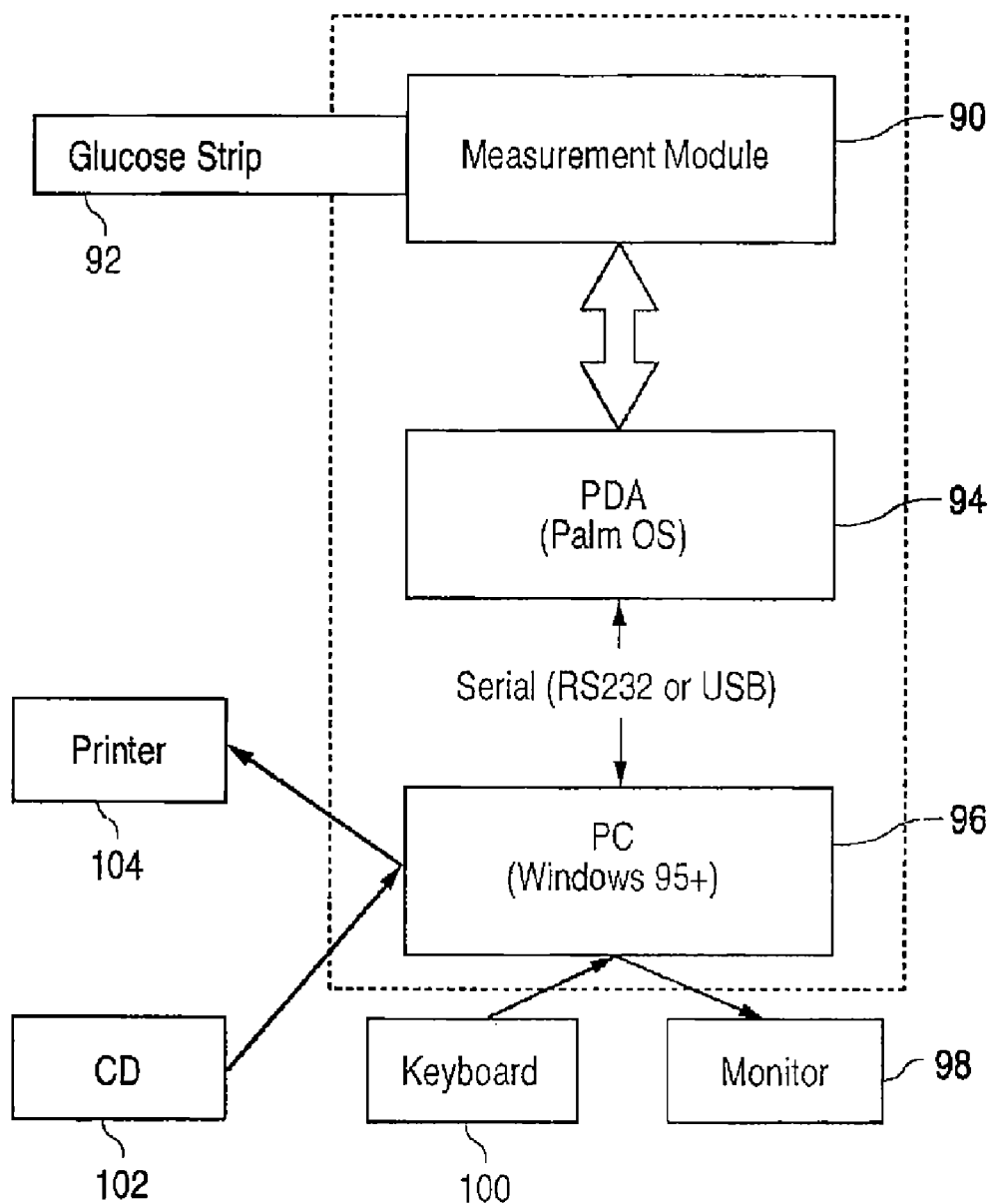
FIG. 8 illustrates a glucose data handling system software according to a preferred embodiment in block diagram=form.

FIG. 8 illustrates generally a glucose data handling system software according to a preferred embodiment in block diagram form. FIG. 8 shows a measurement module 90 which receives a glucose strip 92 for measuring a glucose level of blood applied to the strip 92. The measurement module 90 communicates with the PDA which may be running a Palm operating system or other PDA operating system software. The measurement module 90 is preferably configured to turn off nonessential electronics when no measurement is being made. The measurement module preferably includes a microprocessor that controls internal timing, algorithms, result calculation and fault determination, among other responsibilities. The module 90 includes circuitry to connect the serial output of its internal microprocessor to PDA electronics including a mechanism for program initiation and data transfer. The module 90 also preferably provides electronic ESD protection on analog strip connector lines and flash memory for storage of meter firmware and associated user preferences. The module 90 is preferably powered by the PDA, but could alternatively include its own power source, such as button or AAA-size batteries. The module 90 includes electrical isolation between the strip connector and the HotSync port.

The PDA communicates with a PC when the PDA is preferably HotSynced to the PC. The PDA includes RAM as a temporary database for diabetes management application data and/or programs and non-volatile memory for permanent data and/or program storage. The measurement of the glucose level may however be advantageously performed when the PDA is not HotSynced to the PC, and the PDA includes many data processing features itself for managing data without support from the PC. For example, charts and/or graphs maybe generated on the PDA display. The PC system includes standard peripheral devices such as a monitor 98, keyboard 100, CD-rom 102 and a printer 104.

Figure 9:
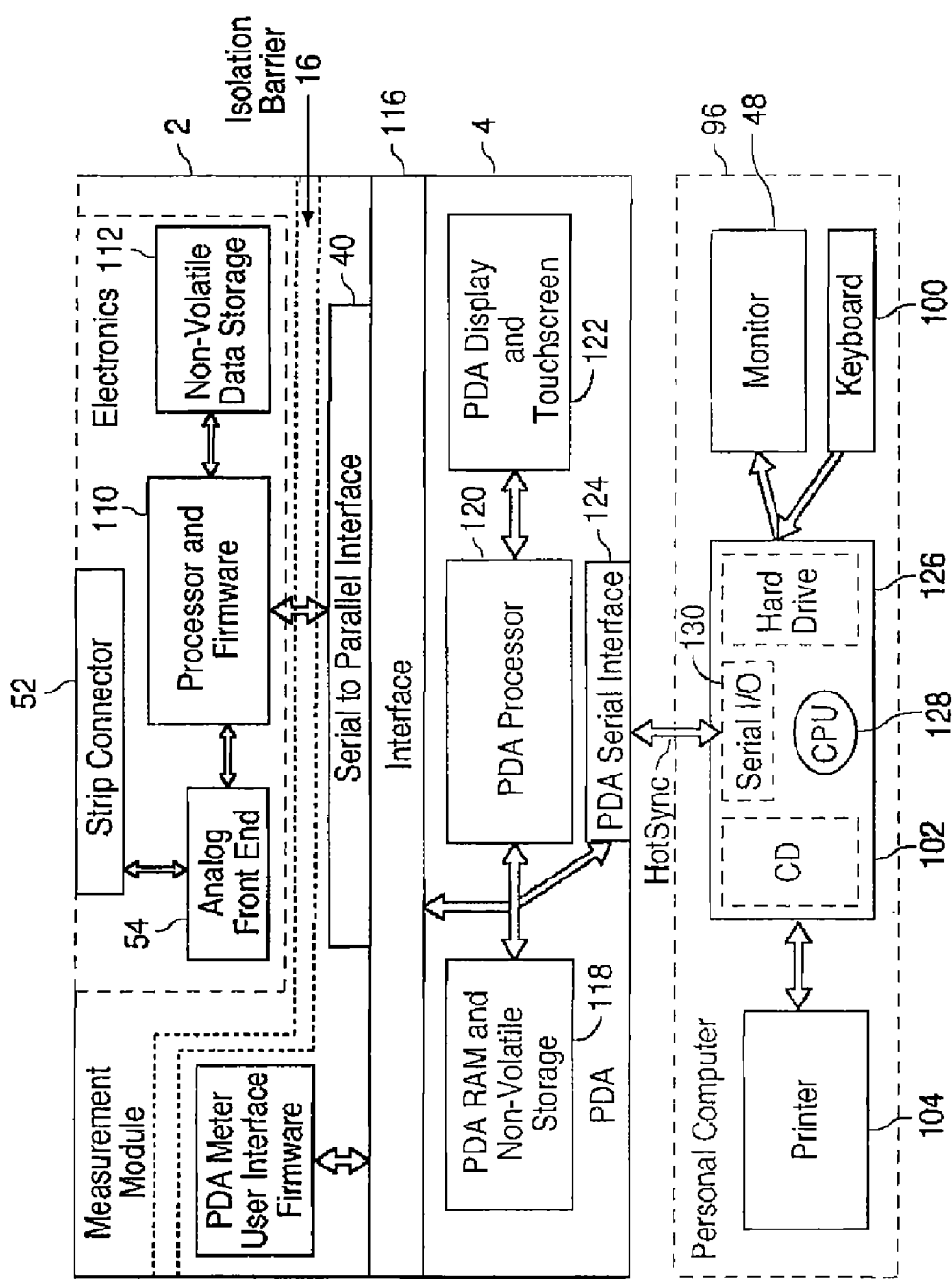
FIG. 9 illustrates a hardware/software block diagram of an integrated glucose measurement module and PDA according to a preferred embodiment.

FIG. 9 illustrates a hardware/software block diagram of an integrated glucose measurement module 2 and PDA 4 according to a preferred embodiment. The measurement module 2 shown includes a strip connector 52 and analog front end electronics 54, such as those shown in FIG. 4. The measurement module 2 also shows a processor running firmware 110, wherein the processor may be as the processor 56 shown in FIG. 4. The processor is shown having access to non-volatile data storage 112. The isolation barrier 16 is shown wherein the above-mentioned components of the measurement module 2, i.e., the strip connector 52, analog front end electronics 54, processor and firmware 110 and nonvolatile data storage 112, are on the isolated side of the barrier 116. PDA meter user interface firmware 114 permits the module 2 to communicate with the PDA 4. A serial to parallel interface, such as that shown in FIG. 2, is also shown in FIG. 9 for converting the serial data transmitted across the barrier 16 using optoisolators 68, 70 such as those described above with respect to FIG. 5. An interface 116 is shown between the module 2 and PDA 4.

The PDA 4 is shown having a PDA RAM and non-volatile storage 118, a PDA processor 120, a PDA display and touch-screen 122 and a PDA serial interface 124. The PDA is configured to HotSync to a PC system 96, such as that described above with respect to FIG. 8, including a monitor 98, keyboard 100, CD-rom 102 and printer 104. The PC system shown in FIG. 9 also includes a hard drive 126, a CPU 128 and a serial I/O 130 which alternatively may be USB.

The data may be entered on the PDA 4. This data may be HotSynced to the PC 96. The data may also be entered on the PC 96 and reverse HotSynced to the PDA 4. In the former case, e.g., the PC 96 would have an application stored in its memory for accepting this data. This PC application would display and print logbook data in various formats. The PC application would also export data to various data processing applications. The application may use a Microsoft Access Database or MDB format, while the data on the PDA may be stored using the Palm PDB format.

The user is preferably able to reverse HotSync data from the PC in order to restore the data to the state it was when it was last HotSynced. The user might want to do this in the event the database on the PDA becomes corrupted. The PC application and database may store a complete history of data that was entered on the PDA. The PDA user may choose to archive some of the PDA data on the PC.

A conduit program may be used. The program may perform the following steps: (1) create a replica of the data stored on the PDA, on the PC; and (2) synchronize data from the PDA to the database on the PC. The two steps may be performed in two separate conduit programs. Synchronizing the data may include reading data from a PDB file and writing it to the PC database. Microsoft Visual Studio may be used for opening, reading and writing data in the PC database. The data may be read from the PDA, matched to data on the PC, format converted, and written to the PC database. Similarly, data entered or modified on the PC may be matched to data on the PDA. The data on the PDA may be updated to reflect the changes made on the PC.

To match data from the PDA to the PC, unique ID numbers may be used in records on the two systems. These ID numbers may be created on the PDA as logbook records or on the PC as logbook entries there. The uniqueness of the ID numbers may be achieved by pre/post fixing the ID with an origin code identifying PC or PDA, or alternatively perhaps a GUID.

To read data from a PDA file and write it to the PC database, it is recognized herein that data in the PC database may be organized into tables, which may be organized into records, which may be broken down into predefined fields. Similarly, at some level data will be organized into records with a consistent field structure on the PDA.

The conduit program reads the data from the PDA file(s) and writes it out to PC tables. The conduit program also reads data from the PC tables and writes them out to PDA file(s). Various types of data conversion may be used. For example, data residing in fields in the PDA file may be converted from the format it exists in the PDA file to a format compatible with the PC and vice-versa. The logical structure of the records in the two systems may be different. Tables may be created (either in code or in an external file such as a database) which define the mapping of data in fields of one system to data in fields in the other. Data may be stored in temporary table(s) that may later be synchronized with main table(s) that contain a complete logbook history, or the conduit program may write to these tables directly.

Figure 10:
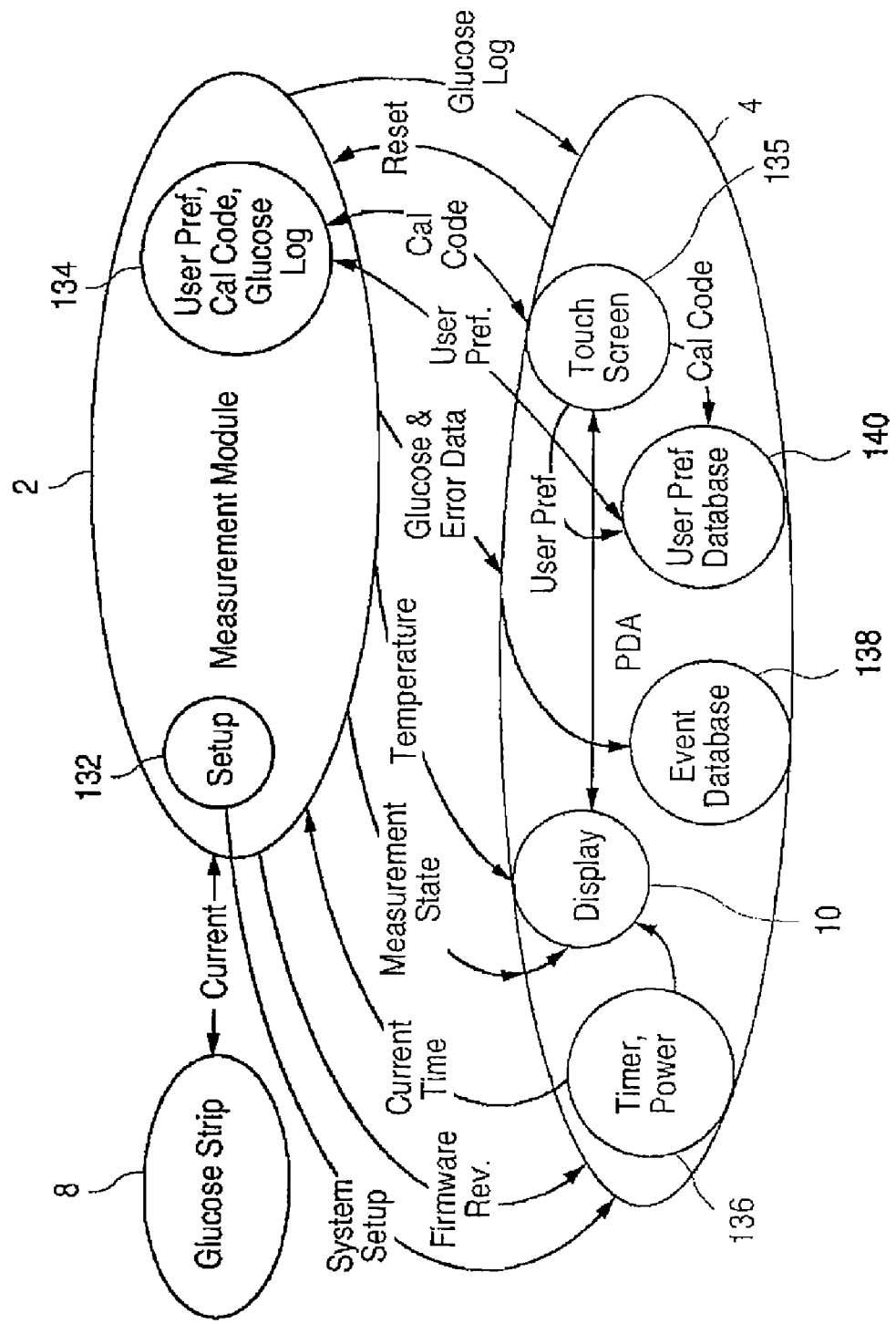
FIG. 10 shows a data flow diagram of an integrated glucose measurement module and PDA according to a preferred embodiment.

FIG. 10 shows a data flow diagram of an integrated glucose measurement module 2 and PDA 4 according to a preferred embodiment. Current is flowed to a strip 8 from the measurement module 2 which, as mentioned, is powered by the PDA 4 as shown and described with respect to FIG. 5. The measurement module 2 includes a setup component 132, which the module 2 communicates to the PDA 4, and a user preferences, calibration code and glucose log component 134. Component 134 serves to convert an electrical reading, such as the current that passes through the blood on the strip 8, to a glucose level, saves a glucose log, saves user preferences, and provides status and error data to the PDA 4. Error data may include glucose errors and charge errors. The PDA 4 is also configured to send user preferences and a calibration code to the measurement module 2 for use or storage by the component 134.

The PDA 4 also receives firmware revision data, measurement state data and temperature data from the measurement module 2. The measurement state and temperature are preferably displayed on a display 10 of the PDA 4 or otherwise provided to a patient by sensory output such as audio or vibration output. The display 10 is preferably also configured to function with touchscreen software and electronics 135. The PDA 4 includes a timer and power module 136, information about which is also displayed. Data regarding the current time is also sent to the module 2 from the timer and power module 136 of the PDA 4.

The PDA advantageously also includes an event database 138 and a user preferences database 140. The event database 138 generally includes information relevant to diabetes management, such as glucose readings. Fields of an event may include time, data, event type. The glucose and error data are stored to the event database 138 after the PDA 4 receives the data from the module 2. The event database includes a logbook which collects glucose, insulin, carbohydrate and exercise data and time. The data in the event database 138 may be graphed in many ways according to helpful default or preprogrammed graphs or according to filtering and preferences inputs from a user. Some exemplary graphs that may be generated on the PDA display 10 from the event database and software loaded on the PDA without the PDA being HotSynced or otherwise connected to a PC or other processing device. In addition, the data including glucose data is automatically sent to the PDA 4 from the module 2 to be stored in the event database 138 where the data can be used to generate graphs that help a user such as a diabetes patient to track glucose and other information. The data measured by the module 2 does not need to be manually entered by the user into a computer before the data can be processed into graphs and the like, or so that the PDA's own software can process or analyze the data to provide useful data analysis to the patient regarding the glucose and other information relating to the condition of the patient. Software on the PDA also preferably includes insulin and carbohydrate tools, and software for communicating with a PC. The user preferences database 140 may store user input such as units of measure, date and time format, an audible or otherwise sensory alert level, the language to be used and other user preferences.

The PC 96 such as that schematically shown at FIGS. 8 and 9 may have additional features. For example, the PC may be configured for viewing and printing the logbook stored on the PDA 4 and transferred to the PDA 4. The PC may be configured to take glucose values and put them into a data management database of its own that may have the same or different capabilities as the event database loaded on the PDA 4. The PC would be helpful for backing-up data and for downloading applications programs to the PDA and also for communicating with other computers over one or more networks. Additional data processing features of the system of the preferred embodiment herein are set forth below with reference to FIG. 11.

Figure 11:
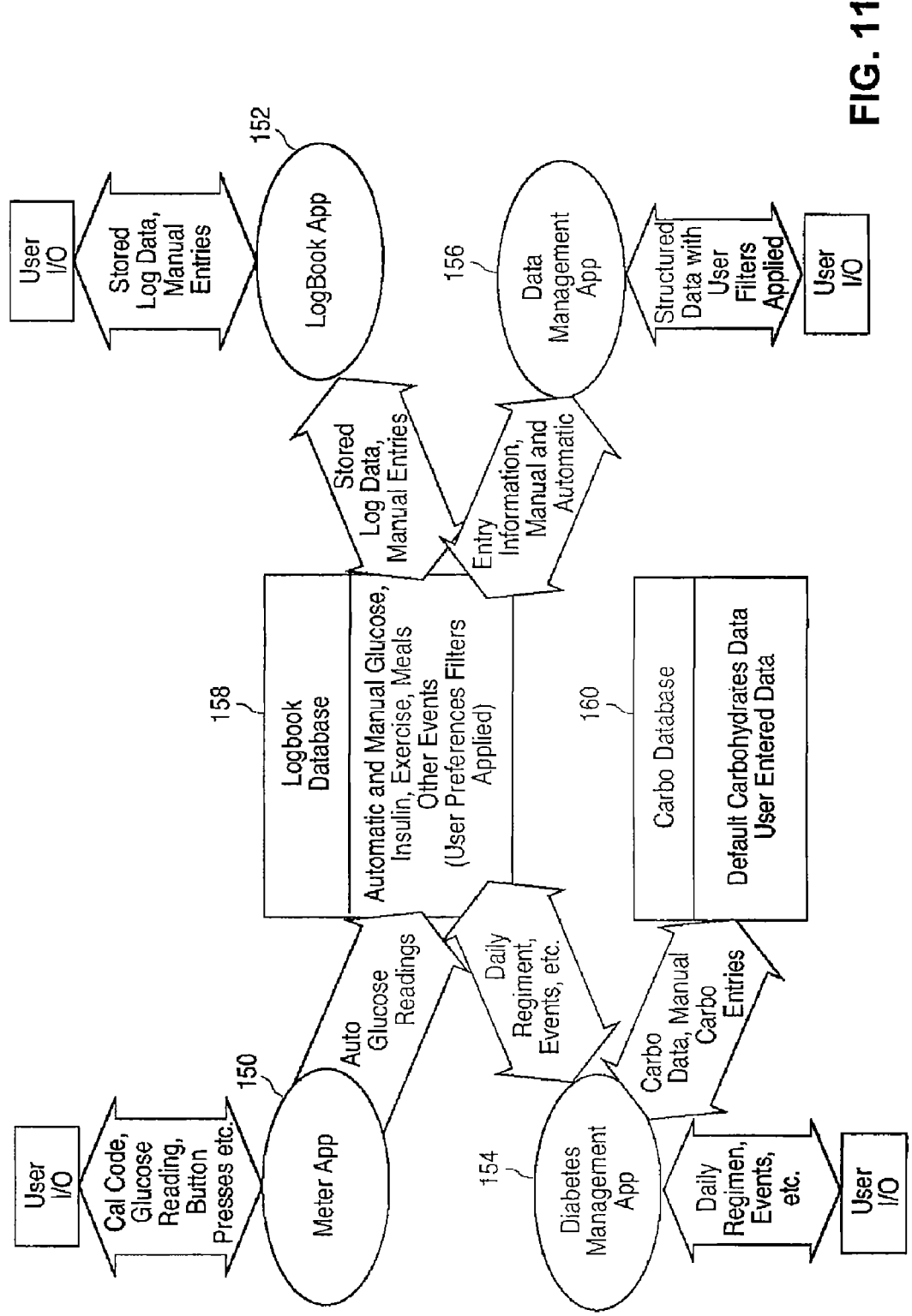
FIG. 11 shows a software data flow diagram of an integrated glucose measurement module and PDA according to a preferred embodiment.

FIG. 11 shows a software data flow diagram of an integrated glucose measurement module 2 and PDA 4 according to a preferred embodiment. FIG. 11 shows how four software applications according to a preferred embodiment interact and illustrate functions of these applications and databases that the applications are programmed to utilize. The applications include a meter application 150, a logbook application 152, a diabetes management application 154 and a data management application 156. Each of these applications preferably runs on the PDA which has been described above (e.g., see FIG. 10). These applications may also each run on a PC to which the PDA is configured to communicate. The applications may be downloaded to the PDA or another device from the PC or a server or other digital data storage device such as a CD-rom or magnetic disk.

FIG. 11 also shows a logbook database 158 and a carbohydrate ("carbo") database 160. The databases 158 and 160 are generally electronic stored records. These may be separate databases or parts of a same database. The logbook and carbo databases may be part of the event database 138 mentioned above with reference to FIG. 10. The logbook database 158 is preferably utilized by each of the applications 150, 152, 154 and 156 mentioned above and shown in FIG. 11, and includes automatic and manual glucose entries, insulin, exercise, meal and other data, and applies user preference filters. The carbo database 160 is preferably utilized by the diabetes management application 154, and includes default carbohydrate data and user entered data. Diabetes management generally refers to activities performed by an individual with diabetes to organize and optimize aspects of life with diabetes such as medication, diet, and exercise that are involved in treating and managing the diabetic condition. The diabetes management application facilitates these activities for the diabetic. The data management application generally provide graphic representations and/or text summaries of data relevant to diabetes management.

The logbook database 158 preferably includes time and date tagged events which are automatically or manually stored such as glucose measurements, manually entered glucose readings, exercise records, insulin injection records, meal time records, state of health records, note records, and medication among others. The user may input entries to the logbook database 158, e.g., that are derived from other glucose meters. Manually entered glucose readings may be flagged as user input rather than meter input. The user may enter other items such as insulin amount, type, and time period, meal times and carbohydrate values, exercise time, type, and degree of exertion (e.g., high, medium, low), state of health, comments and medications. These items may be available to the user from a predefined drop down list that can be edited and added to, or can be manually entered. Data associated with a past event may be entered or modified in the database 158 by the user. Events may be tagged with time periods.

Each application 150-156 is configured to process user inputs including glucose measurements. For example, the meter application is configured to process calibration code input, glucose readings and button presses. The glucose readings are advantageously automatically stored in the logbook database 158 on the PDA according to the programming of the meter application 150. The logbook application 152 is configured to process stored log data and manual entries, and to store and retrieve the log stored log data and manual entries into and from the logbook database 158, respectively. The diabetes management application 154 is configured to process a daily regimen and events such as exercise, meals, insulin dosages and times, etc. and to store and retrieve the daily regimen and events into and from the logbook database 158, respectively. The diabetes management application 154 is also configured to store and retrieve carbo data and manual carbo entries into and from the carbo database 160, respectively. The data management application 156 is configured to process structured data with user filters applied, and to store and retrieve automatic and manual entry information into and from the logbook database, respectively.

The data management application 156 may be configured to allow the user to view data summaries in graphical and text formats. The user may be able to select the length of time to be viewed. The user may also be able to set a default length of time to be viewed from within user preferences. The user may be able to view a complete data set or filter the screen display to show only a selected time period to view. The user may be able to select the event type to be displayed, more than one event type may be selected to be displayed simultaneously. Glucose summary statistics may be displayed by a selected date range and time period. Both selected date range and time period may appear on the display. The summary statistics may include the number of measurements, the highest measurement, the lowest measurement, the average measurement, the standard deviation of the measurements, the percentage of measurements within the target range, the percentage of measurements above the target range, the percentage of measurements below the target range, and insulin and carbohydrate statistics summary. Graphical summaries may also be provided such as line graphs and pie charts (see FIGS. 12-13). The user may be able to select a point on a line graph and see the logbook entry associated with that point.

The diabetes management application 154 may be configured with diabetes management tools such as carbohydrate tables, insulin tables, fast acting carbohydrate list, daily regimen (food and exercise patterns) and target glucose levels. The application 154 may process one or more carbohydrate tables and a food database. The user may be able to choose entries from a database listing carbohydrate values of foods per listed serving size. The user may be able to customize the food database by adding food items to the food database. The user may be able to tag entries as "quick picks". The diabetes management application 154 may include a lookup table containing the dose of insulin required to lower glucose concentration by a known amount. The user may input insulin dosages based on a health care professional's recommendations.

One or more of the applications 150-156 may be configured to issue "alerts". These alerts may be warnings directed to the user that are audible, or otherwise sensory such as by vibration, and displayed with graphics and/or text using the display screen on the PDA. Alerts may indicate that a planned activity is due to begin. Event markers may be used to indicate that the user makes an entry into the logbook 158 to designate a specific condition or incident that relates to a specific blood glucose measurement such as meals, time before or after exercise, medication taken, sickness, feeling hypoglycemic, etc. The applications 150-156, and particularly the diabetes management application 154, may be used for self-monitoring of glucose in whole blood, and may be used by people with diabetes and by healthcare professionals as an aid to monitor the effectiveness of diabetes management.

The applications 150-156, and particularly the meter application 150, may be used to provide direction to a user taking a glucose measurement and control data flow to the logbook 158. For example, when the user inserts a test strip into the module, the module is programmed to check the strip and perform a self test. The display then indicates to the user when to apply the blood. The user then applies the blood sample to the strip. The measurement module monitors for fill (the PDA may, e.g., beep on fill) and takes the measurement. The module is programmed to then determine the glucose level and the PDA displays the result. The glucose value is then automatically entered into the electronic logbook, i.e., without user intervention, and the meter waits for further user input. Once the glucose measurement is complete, the meter application 150 may be configured to relinquish control to one or more of the other applications 152-156.

Figure 12:
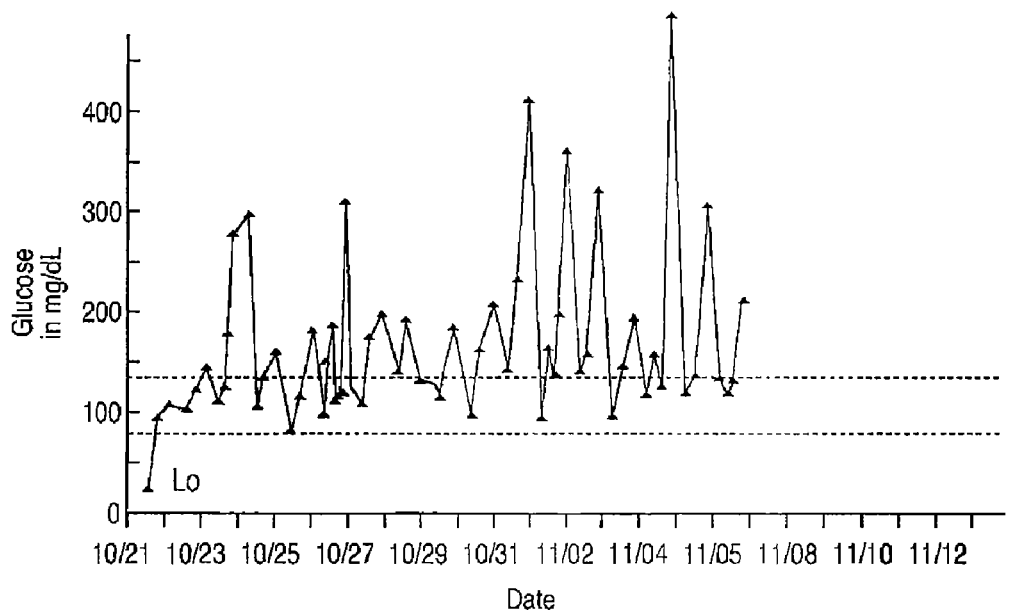
FIG. 12 illustrates a line graph of blood glucose data generated by an integrated measurement module and PDA according to a preferred embodiment.

FIG. 12 illustrates a line graph of blood glucose data generated by an integrated measurement module and PDA according to a preferred embodiment. The data used to generate this graph is stored in the logbook database. The line graph of FIG. 12 shows glucose levels according to the date that the glucose level was taken. As shown, a glucose level that was recorded on November 5 at around 500 mg/dL is labeled as being "Hi" while a glucose level recorded on October 21 at around 20 mg/dL is labeled as "Lo". A range between around 80 mg/dL and 140 mg/dL is indicated by dashed lines in FIG. 12 suggesting an optimal glucose level range.

Figure 13:
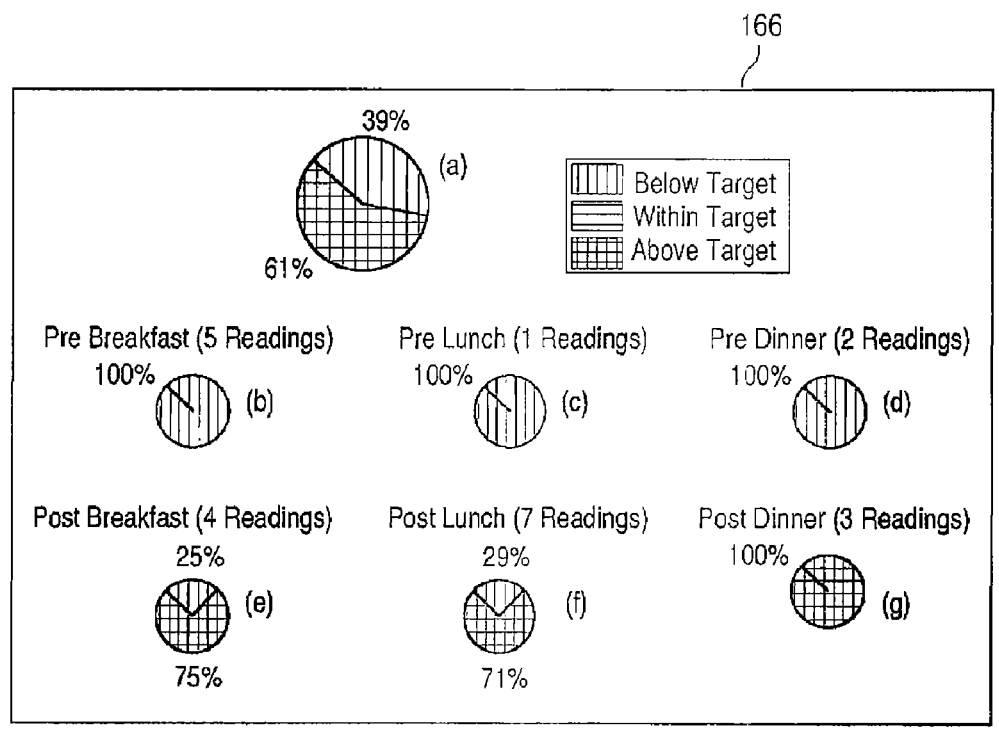
FIG. 13 illustrates pie charts of blood glucose data generated by an integrated measurement module and PDA according to a preferred embodiment.

FIG. 13 illustrates pie charts of blood glucose data generated by an integrated measurement module and PDA according to a preferred embodiment. The data used to generate the illustrative graphs of FIG. 13 is stored in the logbook database. All of the pie charts shown in FIG. 13 may be displayed on a display screen 166 of the PDA at the same time, or one or more may be displayed at a single time. The graphs show the percentage of readings that are below, within or above target. For example, chart (a) shows that overall 39% of the time the readings are within target or within the optimal glucose level range of FIG. 12. Charts (b)-(g) show the percentages of readings that are below, within or above target pre-breakfast, pre-lunch, pre-dinner, post-breakfast, post-lunch and post-dinner, respectively. The user can understand his or her glucose level trends from these graphs.

As described above, the advantageous glucose measurement module 2, as schematically shown, e.g., at FIG. 1, including its rounded-contour, tapered-shape narrowed end portion protruding from an inset shoulder of a connector end, and its composition, facilitates off-finger or alternate site testing. The strip 8, and/or any of various embodiments thereof are described at PCT published application No. WO 01/33216 and U.S. patent application Ser. No. 09/434,026, which are assigned to the same assignee as the present application and are hereby incorporated by reference. For example, the invention may use an electrochemical coulometric test strip such as the Freestyle brand strip sold by TheraSense, Inc. of Alameda, Calif. The Freestyle strip uses a so-called "sidefill" arrangement.

"Coulometry" is the determination of charge passed or projected to pass during complete or nearly complete electrolysis of the analyze, either directly on the electrode or through one or more electron transfer agents. The charge is determined by measurement of charge passed during partial or nearly complete electrolysis of the analyte or, more often, by multiple measurements during the electrolysis of a decaying current and elapsed time. The decaying current results from the decline in the concentration of the electrolyzed species caused by the electrolysis. "Amperometry", another method of electrochemically measuring glucose, includes steady-state amperometry, chronoamperometry, and Cottrelltype measurements.

Another example embodiment is directed to a system that includes several methods of providing immediate contextual feedback to diabetics by connecting to existing technology such as Personal Digital Assistants, (PDAs), and wireless phones. PDAs can store and operate on glucose readings, not only to provide graphs of glucose levels, but to also provide immediate correlation of the glucose level with sleep, exercise, food, and insulin intake and to provide immediate recommendations as to possible steps for better glucose control. Cell phones (or PDAs with wireless connectivity) can transmit glucose reading(s) to a computer network such as the Internet. This allows for immediate verbal and/or written recommendations, retransmission of information to a health care provider either in real time or on a delayed basis, emergency services, and immediate or delayed feedback to others that the diabetic is in control.

Figure 14:
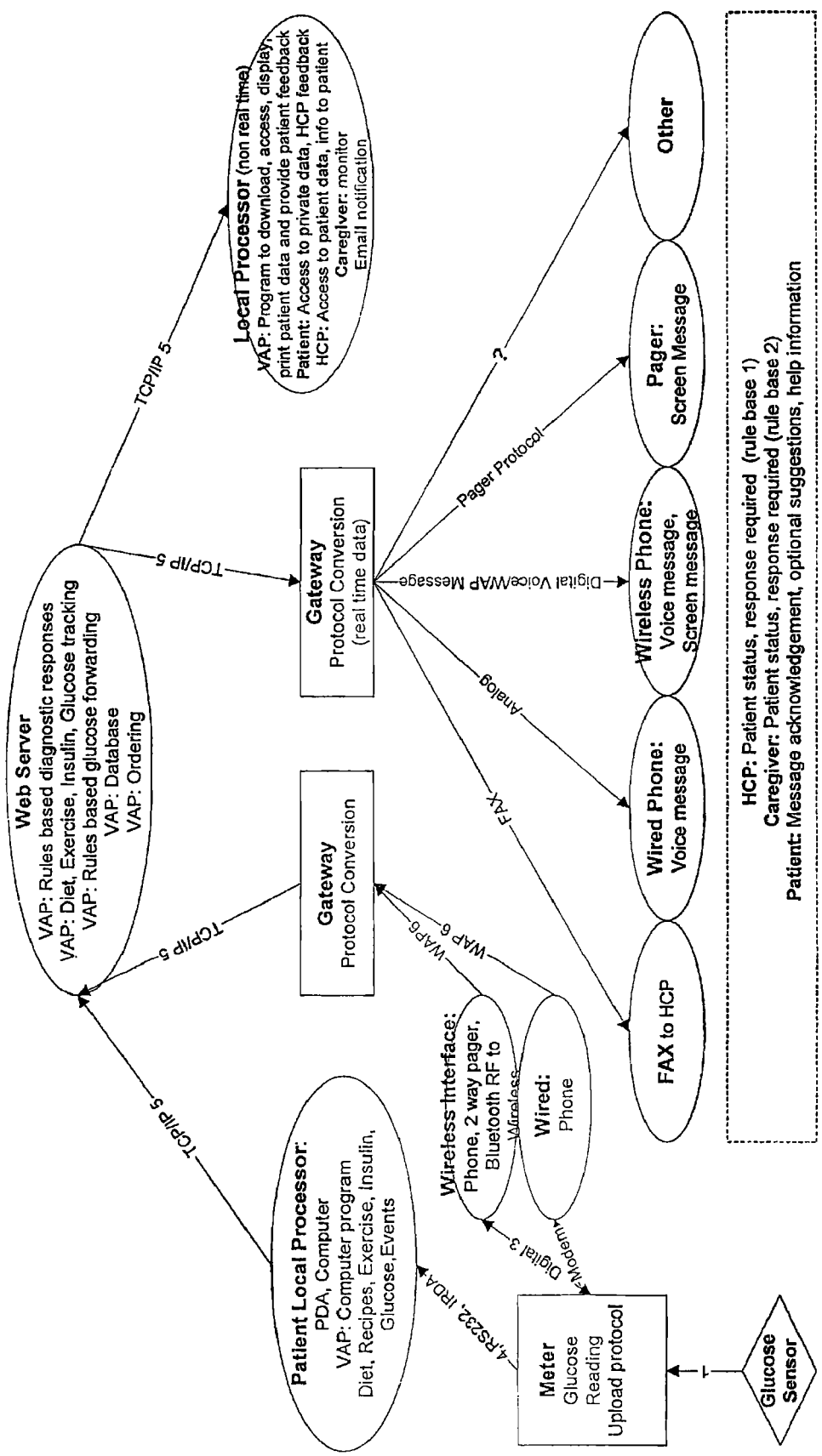
FIG. 14 illustrates a diabetes state processing system according to a preferred embodiment.

To obtain these benefits, the integration from the measurement device to the external device should be seamless and transparent, in other words, a natural extension of use, much the way a VCR and TV work together. Otherwise, the majority of diabetics, despite good intentions, will not be successful in consistently using the system and will not reap the benefits of tight glucose control. A Diabetes Disease State Processing System according to an example embodiment is shown in FIG. 14. This system includes a variety of components which are described below. The system includes a sensor, or more particularly a glucose sensor/measurement device such as the FreeStyle brand (TheraSense, Inc., Alameda, Calif.) glucose strip for single use, or, a continuous (e.g. implantable) blood glucose sensor. The sensor works by breaking down the glucose molecule, releasing an electron for each glucose molecule as is well known in the art. The electrons are measured by a meter and converted to an equivalent glucose reading.

The system of FIG. 14 also includes a meter, or a device that takes the current from the sensor, converts it to an equivalent glucose reading, displays the result, stores it in memory, and connects to other devices to permit the analysis and sharing of data. Also included as part of the system is one or more patient local processors, or personal computers such as a desktop, laptop, palm or other programmable device that has storage and information display capabilities.

The system may also include a wired interface, or more particularly, an interface to a Web Server/Network Node through an existing fixed infrastructure such as phone lines, cable modems, DSL, etc. Additionally, the system may include a wireless interface, or an interface to the Web Server/Network Node through RF or other non-wired media. Several devices are available for this purpose such as, but not limited to, mobile phones, two way pagers, and RF equipped PDAs. Each has one or more frequencies and protocol standards that must be complied with in order to have a successful data transmission. For the purpose of this disclosure, any wireless technology that allows digital communication will suffice. As indicated, the system includes a web server/network node, or a computer on the Internet that contains data and programs to allow other computers to interact with and access its content.

The computer may also include IrDA, or Infrared Data Access, that uses short range, point-to-point non-contact data transmission to move data from one device to another. Further, the system typically may include a gateway, or a computer that takes incoming messages, decodes them, provides protocol conversion and routes them to other processors on the Internet. Further, the system uses one or more protocols, which is the data format used to convey information. Examples of Internet protocols include SMS, TCP, IP and WAR.

Additionally, the system has a local processor, or a computer that is directly accessible and whose data can be modified by the user. Optionally, the system may also incorporate voice recognition technology which allows the input of data through spoken word or the control of a device through spoken word.

Referring again to FIG. 14, data is generated by the glucose transducer sensor system, which converts glucose molecules to electric current or charge, which is then sent to a meter. The meter converts the data to a glucose reading and generates status information. This information is output to a LCD screen and to a standard phone using analog or Bluetooth (RF) technology. The information also may be output digitally to a phone or two way pager. This can be over a IrDA link, or RS232 link, or Bluetooth RF interface. Further, the information may be output to a local processor such as a PC, notebook PC or PDA either using IrDA, RS232, or card type interface. In this case, the data can be augmented by event information, graphed to show trends, and used to generate suggestions as to insulin, food intake, or exercise needed to control blood glucose levels.

In an optional embodiment, the local computer forwards the information using TCP/IP directly to a database on a Web Server/Network Node. The phone connects the information to a gateway programmed to accept the information and forward it using WAP or TCP/IP protocol to a database on a Web Server/Network Node. Similarly, a cell phone or two-way pager forwards the information to a gateway programmed to accept the information and forward it using WAP, TCP/IP or other protocol to a database on a Web Server/Network Node. The system can implement identified protocols in potentially dangerous situations. For example, a global positioning system may be incorporated into or used in conjunction with the system. When glucose readings indicate a hypoglycemic event is possible (e.g., characterized by rapidly falling blood glucose levels) the system can be programmed to generate an emergency call (to a specified care-giver or to an emergency service provider, such as '911') and the GP System will transmit the location of the user as well.

Additionally, in another example embodiment, the Web Server/Network Node Database is programmed to store the data for later viewing in a variety of formats and forward it in real time to a caregiver or HCP using TCP/IP protocol to a gateway. In addition, it can calculate ideal patient actions based upon glucose reading, time since the last meal and insulin dosage and ADA recommendations and send recommendations back to the patient using the original connection.

Messages that are to be forwarded go through a gateway that formats the messages according to the final media: Email, voicemail, pager, facsimile (FAX), or Short Message Service (SMS) and retransmits the messages to their final destination. The caregiver, Health Care Provider (HCP), or patient can access the Web Server/Network Node database through their own local computers to get a recent history of patient information.

In one example embodiment, the control of data may be accomplished in two ways. First, the diabetic (or patient) either provides consent or takes action to transmit data to the Web. Secondly, the retransmission of data is based upon information and rules provided by the patient, caregiver and HCP. As an example, the caregiver may wish to be notified on every reading, on a missed reading, or when the data is outside of a certain range. Likewise, the HCP may wish immediate notification if a patient is known to be out of control and the glucose reading falls outside a given range. It is up to the patient or the caregiver to set up the original forwarding information in conjunction with the HCP's input. The local processor interfaces with the patient's database to supply information as to the message destination, type of message, and forwarding conditions. This would then be frozen under password protection.

In one example embodiment, to ensure that the data is not corrupted, some type of CRC (Cyclic Redundancy Check) or checksum is sent with each message. To prevent electronic eavesdropping, encryption prior to initial transmission may be implemented. As known to those skilled in the art, bluetooth and WAP have built-in encryption methods. For a standard phone link or use of a local processor to transmit a message to the Web Server/Network Node, encryption may be designed into the transmission protocol. Data on the Web Server/Network Node may also be protected from unauthorized copy and dissemination. While the meter serial number may serve as the method to access an individual's data record, additional protection may be required to insure that data can not be used by unauthorized people. Therefore, each person authorized to access the database may have an identification code. This code can limit access to those areas authorized. For an HCP or caregiver, it would be all patients under care plus the rules for automatic data forwarding. A patient or caregiver would be able to access only the meters being used and the rights of other people to access that information. Transfer of data from the database to other computer systems will also be encrypted allowing only the recipient to decrypt it.

Additionally, to manage diabetes, event information may include meal information, insulin information, exercise information and other information, all of which is described as follows. Meal information may include, but is not limited to time since last meal and carbohydrate count. Insulin information may include, but is not limited to insulin dosage, type of insulin, and bolus information. Exercise information may include, but is not limited to time and degree of exercise. other information may include, but is not limited to illness, therapy, and emotional state.

Potential services that may be offered to the diabetic (e.g., patient) as a result of the input event information, include, but are not limited to, reading reminders, notifications, event information, shared data, voice recognition, reading response, reading notification, non-specific glucose recommendation, patient specific glucose recommendation, and real time help.

Figure 15:
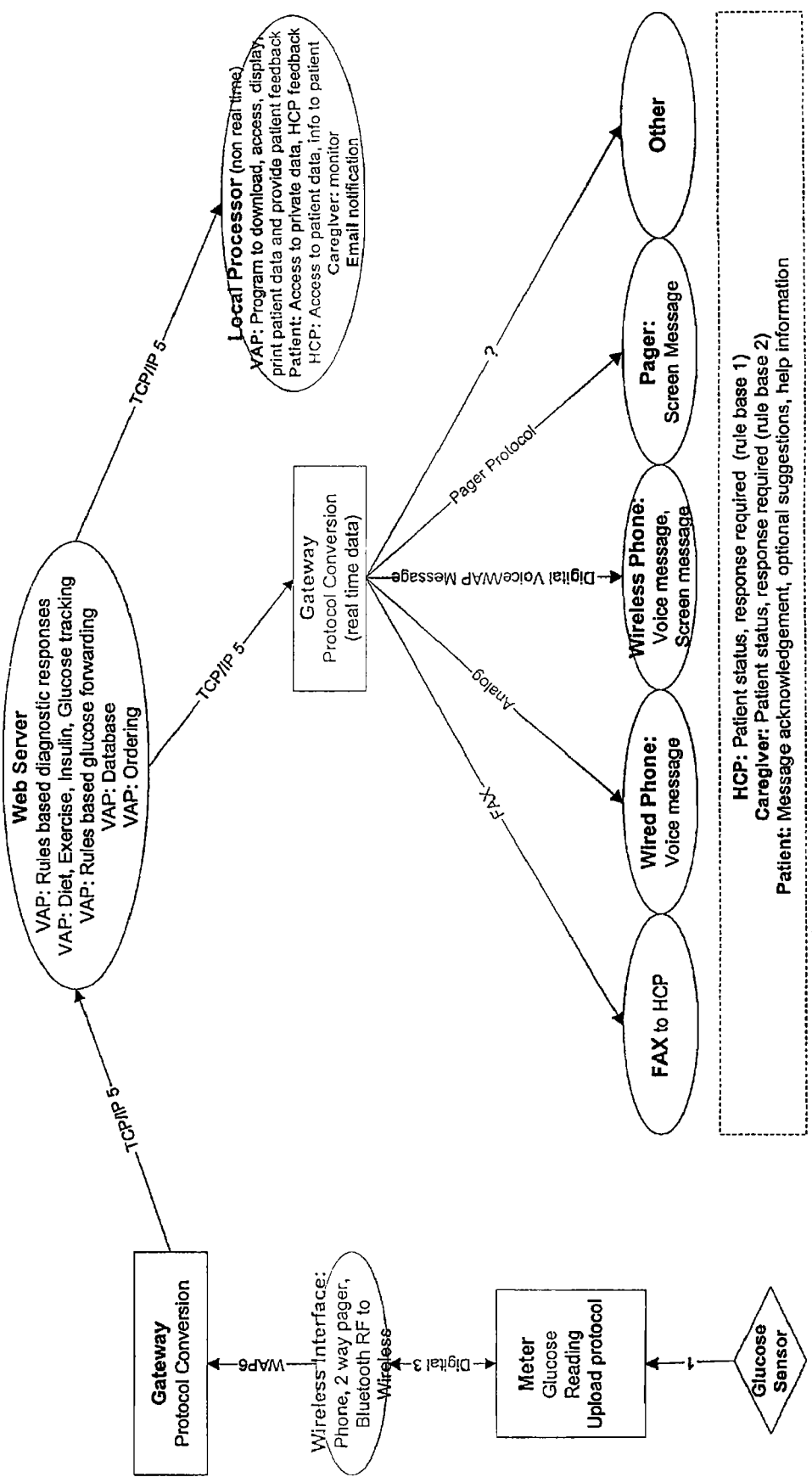
FIG. 15 illustrates wireless diabetes state processing system according to a preferred embodiment.
Figure 16:
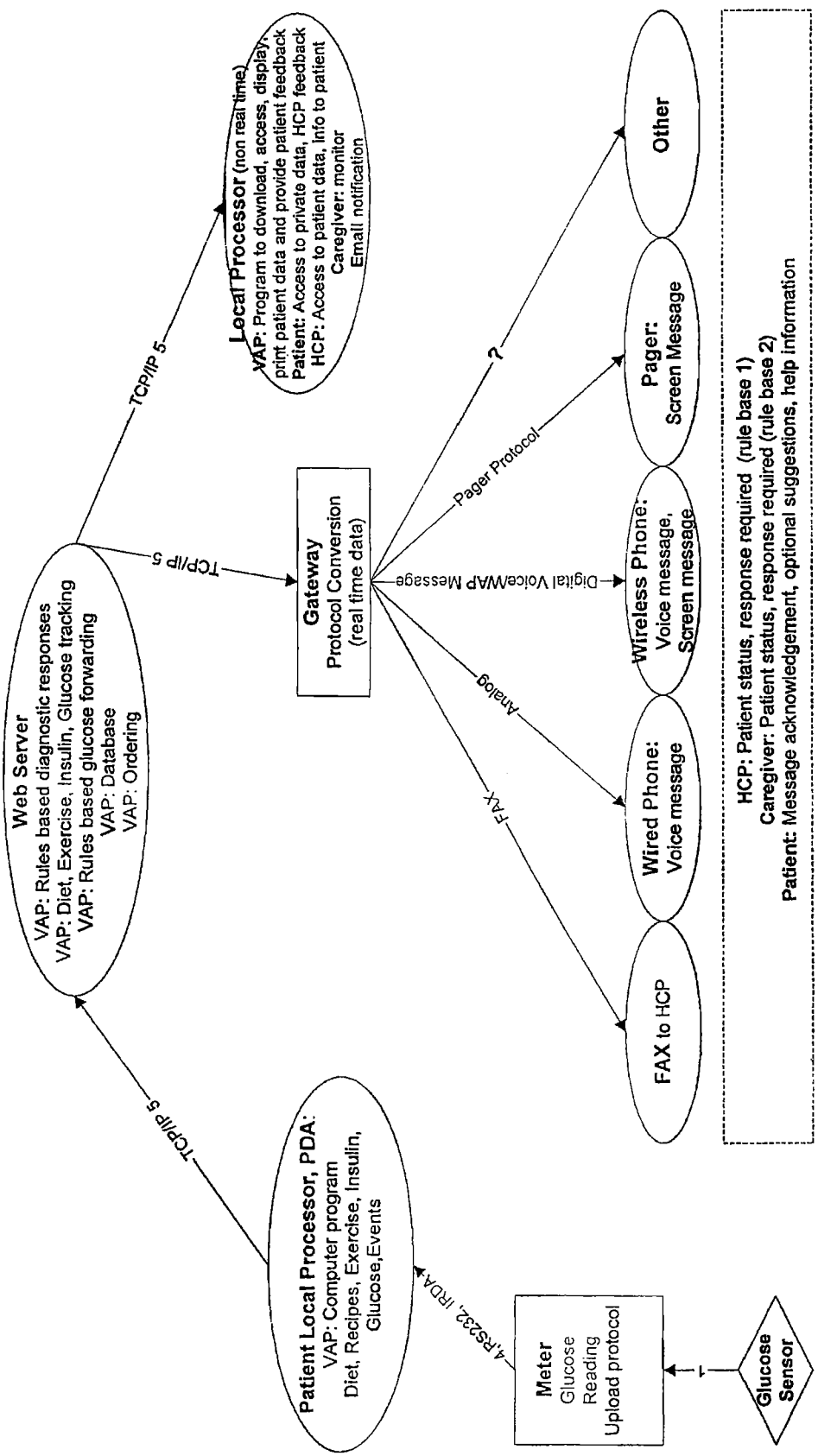
FIG. 16 illustrates a diabetes disease management processing system according to a preferred embodiment.

In another example embodiment, a meter with wireless interface is described. A meter with a wireless interface may be useful for caregivers with children or parents that need assistance with diabetes management. Such a system could also be useful with newly diagnosed diabetics who wish connection to a caregiver or help controlling their disease. The system would also be useful to insurance companies, HMOs, or insulin manufacturers who want to increase active management of the diabetic's glucose. This system consists of a meter tied into a wireless communications system. Variations include a meter having built-in GSM SMS communications that connects to a standard wireless phone over IrDA, RS232 (cable or cradle), or Bluetooth RF link that connect to a standard phone system using a modem or Bluetooth RF link. Referring now to FIG. 15, a schematic of a wireless diabetes disease state processing system is illustrated. The wireless diabetes disease state processing system includes the ability to upload glucose information coupled with voice annotation in real time to a database using a form of encryption. The system further allows for the retransmission of information in real time to a caregiver based upon a set of recipients with specified data formats and rules programmed into the database to provide additional patient assistance. A collection of the glucose information is stored in a database and allows for automated suggestions to improve glucose control. These suggestions can be based upon ADA guidelines or customized by the HCP. Further, the system may optionally provide reminders from the database that a glucose measurement is needed, food intake is required, exercise is required, etc. The system provides the ability of allowing designated individuals, whether they be caregivers, the patient, or a HCP, to review the patient's recent records in a choice of graphical formats. This is done by accessing the database from the reviewers local computer. Alternatively, the database can generate records in a designated format and either send them to the designated individuals by FAX, mail, or electronic mail (email). Additionally, the wireless diabetes disease state processing system provides a way of background checking the database against the meter to ensure that all recent glucose measurements have been uploaded. Further, the system provides a mechanism to designate who has access to the information in the database.

Referring back to FIG. 2, another example embodiment a PDA based glucose meter system is provided and described. In this described embodiment, the meter is fashioned as a module. For example, a "springboard" module sized and shaped to match the HandSpring brand PDA is provided that is able to mate with a PDA to form an analyte monitoring system. A module 2 mates with a PDA 10 thereby permitting a user to interact with the meter using the input mechanisms native to the PDA 10. The modules is fashioned with a receptacle 6 that permits the insertion of a sensor 8. Software necessary for the display and analysis of the analyte level information is contained in the memory unit of the PDA 10. Accordingly, the module 2 uploads analyte level information to the PDA 10, so that the software contained therein can operate upon the information, and present the information to the user in a meaningful and useful fashion. For example, the PDA 10 may be programmed to display a chart of analyte levels upon which event markers indicating meals and exercise are indicated. Other examples of the functionality provided by the software/firmware on the PDA include, but are not limited to an electronic logbook, a data management tool providing graphic representation and/or textual summaries of data relevant to the monitoring and/or control of the analyte level being monitored, and a diabetes management tool for informing a user about all aspects of activities regarding managing diabetes.

In some embodiments, the module 2 may also include an RF receiver and antenna to permit the module to receive a transmission containing information regarding the analyte level of a patient's bodily fluid. This information may be automatically entered in the electronic logbook. In one system embodiment, such a transmission emanates from an analyte-sensing system affixed to a patient and configured with a transmitter. Optionally, the analyte-sensing system may initiate such a transmission periodically, thereby providing the PDA/meter unit with a series of analyte level information, which may be related temporally by either the processing circuitry of the module 2 or of the PDA 10. In still other embodiments, the module 2 contains circuitry permitting the module 2 to transmit information to a remote computer, or the like. Alternatively, the PDA 10 may uplink the information to a home computer, or the like.

The normal user input/output mechanisms of the PDA 10 may be utilized by the user/patient. By making use of these mechanisms (such as a touch screen input mechanism), the user/patient may indicate the occurrence of certain events likely to impact the level of the particular analyte being monitored. For example, the user/patient may indicate that the patient just had a meal or just engaged in exercise. To assist a user/patient in entering such event data, the PDA may be programmed to provide drop-down menus that include common forms of insulin that the patient may have taken. A drop down menu may also include options to automatically note breakfast, lunch, dinner, snack, bedtime, or sleep in the electronic logbook. Other drop down menus may permit the patient to note the presence of a cold/virus, high stress, fatigue, a large meal, alcohol, fever, or depression. The patient may also select self-customized meal lists or select a carbohydrate counter function. The PDA may use its built-in alarm capabilities to alert the user/patient of certain activities that are to take place, such as taking of insulin, testing of blood sugar, eating of a meal, and exercise.

The system of the invention may be useful to insurance companies, HMOs, or insulin manufacturers who want to increase active management of the diabetic's glucose, or may be used by adults who wish to combine diabetes management with other aspects of their lives. This system consists of a coulometer with glucose strip interface and optionally a digital RF link (or other type of data link) to a continuous glucose sensor. These components are integrated with the PDA using either a module that plugs into the PDA or a RS232 link tied to the PDA's hot sync interface. In order to manipulate the glucose strip to place it on the blood drop, the connector must be placed in such a way that the PDA's body does not interfere with placement. This can be accomplished by having the strip interface telescope outward, either by having the complete module extend, just a portion of it, or include the strip connector at the end of a flexible cable. Power to run the coulometer may come from the PDA itself. Alternatively, a standard FreeStyle brand or other brand of blood glucose meter can interface directly to a PDA using, e.g. an IrDA interface. The meter can connect to the PDA using a docking station approach, connect via a three conductor RS232 cable, or use the IrDA interface.

The diabetes disease management processing system provides real time feedback and data entry capabilities to the diabetic for self-control. The system provides for the ability to annotate glucose measurements with event information turning the PDA into the diabetics log book. Further, the system allows for the upload of glucose and event information to a database server through either the PDA's wireless interface or by hot syncing through a computer into the database. Once in the database, the information is available to a HCP as in the example above. The system also permits optional reminders to be sent from the database of a meter that a glucose measurement is needed, food intake is required, exercise or insulin is required, etc. Additionally, the system provides for the ability to graph the glucose data in one of several formats. Further, the system also allows for the ability to combine event data with the glucose data in a graphical format to provide an overall view of the major influences on glucose levels. This makes it easier for the diabetic to see the results of daily activities on glucose levels. Recommendations can be calculated based upon event, glucose, and ADA or other health care provider guidelines and then presented to the diabetic. Further, the system provides for the ability to update the program by downloading more recent versions of software via particular website access.

In an additional embodiment for disseminating data representing a level of an analyte in a bodily fluid, the system comprises an analyte sensor configured and arranged to detect the level of the analyte in the bodily fluid. Additionally, the system comprises a processing device configured and arranged to respond to the detection of the analyte by producing data representing the level of the analyte in the bodily fluid. The processing device is also configured and arranged to transmit the data to and/or across a network. Finally, the system comprises a server, accessible via the network. The server is configured and arranged to receive the data representing the level of the analyte in the bodily fluid. Further, the server is configured and arranged to create a presentation of the data and to translate the presentation into a semantic representation (such as HTML).

An additional embodiment of the invention disclosed herein is a system for detecting a level of an analyte in a bodily fluid of a patient and transmitting data representing the level of the analyte to a remote processing device. The system comprises an analyte sensor configured and arranged to detect the level of the analyte in the bodily fluid. Additionally, the system comprises an analyte monitor configured and arranged to receive the analyte sensor and to respond to the detection of the analyte by producing analyte data representing the level of the analyte in the bodily fluid. The analyte monitor is also configured and arranged to receive event data regarding the occurrence of an event affecting the level of the analyte in the patient. The analyte monitor is further configured and arranged to temporally relate the analyte data and the event data. Optionally, the processing device is configured and arranged to modulate a radio frequency signal with the analyte data and the event data and to transmit the modulated signal through the atmosphere to a remote processing device.

While exemplary drawings and specific embodiments of the present invention have been described and illustrated, it is to be understood that that the scope of the present invention is not to be limited to the particular embodiments discussed. Thus, the embodiments shall be regarded as illustrative rather than restrictive, and it should be understood that variations may be made in those embodiments by workers skilled in the arts without departing from the scope of the present invention as set forth in the claims that follow, and equivalents thereof.

In addition, in the method claims that follow, the steps have been ordered in selected typographical sequences. However, the sequences have been selected and so ordered for typographical convenience and are not intended to imply any particular order for performing the steps, except for those claims wherein a particular ordering of steps is expressly set forth or understood by one of ordinary skill in the art as being necessary.

What is claimed is:

1. A system for managing treatment of a particular health condition afflicting a patient, the system comprising:
   a remote web server system connected to and controlling access to a database, wherein the web server system is accessible by multiple authorized users and stores multiple patient data sets, wherein the multiple patient data sets include patient health condition data received from a respective patient, and the web server system is configured to receive and transmit patient data;
   a patient local processing device configured to connect to the web server system via a network connection, the patient local processing device comprising a display, a communication port, an input device, a processor, a non-volatile memory, and a health management program stored on the memory and configured to manage treatment of a particular health condition, wherein the processor is configured to access the memory, load into the processor and run the health management program which programs the processor to:
   control the display of the patient local processing device to issue a visual prompt for entry of patient health condition data, including subjective patient symptom data in a predefined drop-down list of subjective symptoms that may be individually selected and entered as data with the input device, and medication delivery data, and to issue a prompt reminding the patient of a planned activity;
   receive patient health condition data related to a particular health condition afflicting a patient, including analyte level data with associated times at which the analyte level data were taken from a patient, and further including subjective patient symptom data with associated times at which the symptoms were experienced from the predefined drop-down list, via the input device;
   store the received patient health condition data, including subjective patient symptom data, in the memory of the patient local processing device along with the times associated with the data, so that analyte data may be associated with subject data at the same or relevant times to determine any possible influences of subjective symptoms on analyte levels; and
   send selected stored patient health condition data to the remote web server system for central storage in the database connected to the web server system, wherein the stored data is accessible by multiple authorized users.

2. The system of claim 1, wherein the particular health condition afflicting a patient is diabetes.

3. The system of claim 1, wherein the health management program further programs the processor of the patient local processing device to issue a prompt as one of a visual prompt, auditory prompt, vibratory prompt and any combination thereof.

4. The system of claim 1, wherein the database of the web server system is accessible by authorized users having identification codes.

5. The system of claim 1, wherein the authorized multiple users include at least one of a caregiver, patient and healthcare provider.

6. The system of claim 1, wherein the web server system is configured to automatically forward data stored in the database to an authorized healthcare provider of a respective patient.

7. The system of claim 1, wherein the web server system is configured to retransmit received data in accordance with information and rules provided by at least one of a patient, caregiver and healthcare provider.

8. The system of claim 1, wherein selected patient health condition data sent to the web server system database is automatically forwarded to a healthcare provider in real time.

9. The system of claim 1, wherein a selection of the patient health condition data stored in the database connected to the remote web server system is forwarded to a healthcare provider on a delayed basis.

10. The system of claim 1, wherein the patient local processing device comprises a hand-held computing device.

11. The system of claim 1, wherein the patient local processing device comprises one of a personal computer, desktop, laptop, mobile phone and PDA.

12. The system of claim 1, wherein the health management program further programs the processor of the patient local processing device to control the display to present an additional pre-defined drop-down list having a list of options from which a patient can select an option in response to a prompt for entry of patient health condition data.

13. The system of claim 12, wherein the additional drop-down list includes a list of options related to medications.

14. The system of claim 12, wherein the additional drop-down list includes a list of options related to daily activities affecting the disease afflicting the patient.

15. The system of claim 1, wherein the web server system further comprises a processor connected to the database, wherein the processor is programmed to generate records in a designated format and send the generated records to a designated recipient by at least one of facsimile, mail and email.

16. The system of claim 1, wherein the health management program further programs the processor of the patient local processing device to receive patient health condition data only via manual entry of the input device.

17. A system for managing treatment of a particular disease afflicting a patient, the system comprising:
a remote web server system comprising a database, wherein the web server system stores multiple patient data sets in the database, and the multiple patient data sets include patient health condition data received from respective patients, and the web server system is configured to receive and transmit patient data; and wherein the database is accessible by multiple authorized users;
a patient local processing device configured to connect to the web server system via a network connection, the patient local processing device comprising a display, a communication port, an input device, a processor, a non-volatile memory, and a health management program stored on the memory and configured to manage treatment of the particular disease, wherein the processor is configured to access the memory to load into the processor and run the health management program which programs the processor to:
control the display of the patient local processing device to present a prompt for entry of patient health condition data related to a particular disease afflicting a patient, including symptom data, subjective patient health condition data in the form of a predefined drop-down list of subjective symptoms that may be individually selected and entered as data with the input device, and medication delivery data, and to present a visual prompt reminding the patient of a planned activity;
receive patient health condition data via the input device, including analyte level data with associated times at which the data were taken from a patient, and further including a selection of subjective symptom data from the drop-down list via the input device;
store the received patient health condition data, including selected subjective symptom data, along with the times associated with the data in the memory of the patient local processing device;
compile the stored patient health condition data into a data summary in which analyte levels at specific times are associated with subjective patient symptom data at specific times so that the summary shows an overall view of possible influences of subjective patient symptoms on analyte levels; and
automatically forward the compiled data summary from the patient local processing device to a healthcare provider via the web server system.

18. The system of claim 17, wherein the particular health condition afflicting a patient is diabetes.

19. The system of claim 17, wherein the health management program further programs the processor to issue a prompt as one of a visual prompt, auditory prompt, vibratory prompt and any combination thereof.

20. The system of claim 17, wherein the health management program further programs the processor to generate reports in a pre-designated format.

21. The system of claim 17, wherein the compiled data summary sent to the web server system is automatically forwarded to the healthcare provider in real time.

22. The system of claim 17, wherein the compiled data summary sent to the web server is stored in the database connected to the remote web server system, and is automatically forwarded to a healthcare provider on a delayed basis.

23. The system of claim 17, wherein the compiled data summary is automatically transmitted to a healthcare provider in accordance with information and rules provided by the patient.

24. The system of claim 17, wherein the patient local processing device comprises one of a personal computer, desktop, laptop, and PDA.

25. The system of claim 17, wherein the health management program further programs the processor of the patient local processing device to control the display to present an additional pre-defined drop-down list having a list of options from which a patient can select an option in response to a prompt for entry of patient health condition data.

26. The system of claim 25, wherein the additional drop-down list includes a list of options related to medications.

27. The system of claim 25, wherein the additional drop-down list includes a list of options related to daily activities affecting a disease afflicting a patient.

* * * * *